(12) United States Patent
Solomon et al.

(10) Patent No.: US 7,318,935 B2
(45) Date of Patent: *Jan. 15, 2008

(54) PHARMACEUTICAL TABLETS WITH ACTIVE AND INACTIVE SEGMENTS

(75) Inventors: Lawrence Solomon, Boca Raton, FL (US); Allan S. Kaplan, Boca Raton, FL (US)

(73) Assignee: ACCU-BREAK Technologies, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/693,059

(22) Filed: Mar. 29, 2007

(65) Prior Publication Data
US 2007/0190147 A1    Aug. 16, 2007

Related U.S. Application Data

(63) Continuation-in-part of application No. 11/569,343, filed as application No. PCT/US2005/018633 on May 23, 2005, application No. 11/693,059, which is a continuation-in-part of application No. 10/598,267, filed as application No. PCT/US2005/018638 on May 23, 2005, application No. 11/693,059, which is a continuation-in-part of application No. 10/598,306, filed as application No. PCT/US2005/018639 on May 23, 2005, application No. 11/693,059, which is a continuation-in-part of application No. 10/598,315, filed as application No. PCT/US2005/018631 on May 23, 2005, application No. 11/693,059, which is a continuation-in-part of application No. 10/598,344, filed as application No. PCT/US2005/018632 on May 23, 2005.

(60) Provisional application No. 60/573,042, filed on May 21, 2004, provisional application No. 60/573,134, filed on May 21, 2004.

(51) Int. Cl.
*A61K 9/20* (2006.01)
*A61K 9/44* (2006.01)
*A61K 9/22* (2006.01)
*A61K 9/24* (2006.01)

(52) U.S. Cl. ............... 424/464; 424/465; 424/467; 424/468; 424/472; 424/473

(58) Field of Classification Search ............ None
See application file for complete search history.

(56) References Cited

U.S. PATENT DOCUMENTS 3,128,226 A    4/1964    Rubin et al.
5,061,494 A  * 10/1991    Ni et al. ............. 424/467

(Continued)

OTHER PUBLICATIONS

H.A. Lieberman and L. Lachman, Pharmaceutical Dosage Forms, vol. 1, pp. 217-223, Marcel Dekker, Inc., New York, New York.

*Primary Examiner*—Lakshmi S. Channavajjala
(74) *Attorney, Agent, or Firm*—Ted W. Whitlock

(57) ABSTRACT

An immediate release compressed pharmaceutical tablet that has two or more segments and a top and a bottom and has a height that exceeds the width of the tablet. The height is measured vertically from the top to the bottom of the tablet while it is in the tablet die in which it is fully compressed, after compression has been completed. The width is measured as the greatest horizontal dimension of the tablet at a location halfway between the top and the bottom of the tablet, except that when the horizontal cross-section of the tablet is substantially rectangular, the width is defined by locating the two shorter sides of the perimeter of the horizontal cross-section, and measuring the length of a line that is at right angle to the shorter sides.

11 Claims, 9 Drawing Sheets

U.S. PATENT DOCUMENTS

| | | | |
|---|---|---|---|
| 5,487,901 A * | 1/1996 | Conte et al. | 424/472 |
| 5,817,340 A | 10/1998 | Roche et al. | |
| 6,086,919 A | 7/2000 | Bauer et al. | |
| 6,183,778 B1 | 2/2001 | Conte et al. | |
| 6,294,200 B1 | 9/2001 | Conte et al. | |
| 6,309,668 B1 | 10/2001 | Bastin et al. | |
| 6,919,373 B1 | 7/2005 | Lam et al. | |
| 7,011,849 B2 | 3/2006 | Storm et al. | |
| 2002/0132850 A1 | 9/2002 | Bartholomaus | |
| 2005/0013863 A1* | 1/2005 | Lim et al. | 424/472 |
| 2005/0038039 A1 | 2/2005 | Fanara et al. | |
| 2006/0280794 A1 | 12/2006 | Hamaguchi et al. | |

\* cited by examiner

PHARMACEUTICAL TABLETS WITH ACTIVE AND INACTIVE SEGMENTS

CROSS-REFERENCE TO RELATED APPLICATIONS

This is a continuation-in-part of pending U.S. patent application Ser. No. 11/569,343 filed Nov. 17, 2006 pursuant to 35 USC 371 as a national stage application from PCT/US05/18633 filed May 23, 2005 which claims priority to U.S. Provisional Appl'n Ser. No. 60/573,042, filed May 21, 2004 and U.S. Provisional Appl'n Ser. No. 60/573,134 filed May 21, 2004.

This is also a continuation-in-part of pending U.S. patent application Ser. No. 10/598,267 filed Aug. 23, 2006 pursuant to 35 USC 371 as a national stage application from PCT/US05/18638 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

This is also a continuation-in-part of pending U.S. patent application Ser. No. 10/598,306 filed Aug. 24, 2006 pursuant to 35 USC 371 as a national stage application from PCT/US05/18639 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

This is also a continuation-in-part of pending U.S. patent application Ser. No. 10/598,315 filed Aug. 24, 2006 pursuant to 35 USC 371 as a national stage application from PCT/US05/18631 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

This is also a continuation-in-part of pending U.S. patent application Ser. No. 10/598,344 filed Aug. 24, 2006 pursuant to 35 USC 371 as a national stage application from PCT/US05/18632 filed May 23, 2005 which claims priority to U.S. Provisional Appl'n Ser. No. 60/573,042 filed May 21, 2004 and U.S. Provisional Appl'n Ser. No. 60/573,134 filed May 21, 2004.

Each of the above patent applications is hereby incorporated by reference in its entirety, as applicable.

FIELD OF THE INVENTION

The single invention described herein concerns immediate release, segmented and non-homogeneous compressed pharmaceutical tablets having at least two different active pharmaceutical ingredients contained within a single dosage form.

BACKGROUND

Pharmaceutical tablets in divisible form containing an indentation known as a score have long been known and widely used. Problems with breaking scored tablets are well-known. These problems include loss of active drug and inaccurate division of the tablet, so that a tablet intended to be divided into two equal half-tablets often does not come close to that ideal.

Many drugs, such as warfarin, require dosage adjustments and are frequently broken. These dosage adjustments through tablet breaking by patients have been determined to be imprecise. As the following discussion demonstrates, for many years experts have called upon the pharmaceutical industry to improve the quality of tablet breaking, but limited attention has previously been paid to these calls by the pharmaceutical industry.

In 1984, Stimpel et al. ("Stimpel") described the relative accuracy of breaking of various tablets for treatment of cardiovascular problems. M, Stimpel et al. "Breaking Tablets in Half." *The Lancet* (1984):1299. Even though breaking was performed by a sophisticated, dexterous person, Stimpel found that breaking was not accurate, and opined that real world use by patients would provide yet more unsatisfactory results. Stimpel called upon the pharmaceutical industry to improve the accuracy of splitting tablets: "Clearly any assumption that halving a tablet will not lead to inaccurate doses is invalid. This potential source of inaccuracy could be even more significant in clinical situations (our study was done tinder ideal conditions) and the pharmaceutical industry should tackle it, either by improving divisibility (as already has been done for Lopressor and Logroton) or, even better, by marketing a wider range of unscored tablets to provide all the doses that might be indicated clinically."

Despite that finding and despite the subsequent issuance of various patents relating to optimizing a scoring pattern and/or tablet shape, Rodenhuis et al., (2004) noted that: "Improving the functioning of score lines may be a more practical approach than banning this dosage form" (emphasis added). N. Rodenhuis et al., "The rationale of scored tablets as dosage form." *European J. of Pharmaceutical Sciences* 21 (2004):305-308 (hereafter "Rodenhuis"). Rodenhuis observed that European regulatory authorities started a policy to discourage scoring of tablets in 1998. This policy change, according to Rodenhuis, was likely due to "many recent reports of bad functioning score lines" in tablets that are "difficult to break," and that "show unsatisfactory mass uniformity of the subdivided halves." The authors further describe useful aspects of scoring tablets. For a comprehensive review article on this topic, see van Santen, F., Barends, D. M. and Frijlink, H. W. "Breaking of scored tablets: a review." *European J. of Pharmaceutics and Biopharmaceutics* 53 (2002): 139-145.

Some current studies that demonstrate the severity of the problem are described below: Peek et al., (2002), studied tablet splitting by "elderly patients" aged 50-79. Peek, B. T., Al-Achi, A., and Coombs, S. J., "Accuracy of Tablet Splitting by Elderly Patients" *The Journal of the American Medical Association* 288 No. 4 (2002):139-145. Breaking scored tablets with mechanical tablet splitters without specific instruction led to unsatisfactory separation of the tablets. For example, warfarin 5 mg was, on average, split into 1.9 and 3.1 mg tablet halves. This potent anticoagulant has such a narrow therapeutic range that 2, 2.5, and 3 mg tablet doses are manufactured. Biron et al., (1999), demonstrated that warfarin 10 mg also often split to less than 4.25 or greater than 5.75 mg tablet halves. Biron, C., Liczner, P. Hansel, S., and Schved, J. F., "Oral Anticoagulant Drugs: Do Not Cut Tablets in Quarters." *Thromb Haemost* 1201 (1999). In addition, they demonstrated that loss of mass due to crumbling or chipping from the breaking of the warfarin tablets was statistically significant. They also demonstrated that quartering of the tablets was grossly inaccurate.

McDevitt et al., (1998), found that 25 mg scored hydrochlorothiazide tablets were manually split badly enough that 12.4% deviated by more than 20% from ideal weight. McDevitt, J. T., Gurst, A. H. and Chen, Y., "Accuracy of Tablet Splitting," *Pharmacotherapy* 18 No. 1 (1998):193-197.

Rosenberg et al., (2002), studied pharmacist-dispensed split tablets. Rosenberg. J. M., Nathan, J. P. and Plakogiannis, F., "Weight Variability of Pharmacist-Dispensed Split Tablets" *Journal of American Pharmaceutical Association* 42 No. 2 (2002):200-205. They found that "tablet splitting resulted in an unacceptably high incidence of weight variation."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopeia) uniformity test . . . The practice of dividing tablets to save costs or to improve a dosage regimen . . . is not recommended for patients using drugs with more substantial toxicity and steep dose-response efficacy curves." Teng, J., Song, C. K., Williams, R. L. and Polli, J. E., "Lack of Medication Dose Uniformity in Commonly Split Tablets." *Journal of American Pharmaceutical Association* 42 No. 2 (2002):195-199.

Rodenhuis reported that 31% of all tablets in one Netherlands study were subdivided before being swallowed. In the U.S., "managed care" insurance organizations, the Veterans Administration and others may encourage splitting by patients of unscored tablets that may not even have symmetrical shapes. Many drug products in the US either are unscored tablets, or are provided as capsules despite being able to be produced as tablets.

The invention is directed to amelioration of the problems described above. The subject invention may allow either a single agent or a mixture of two active agents (i.e., one or, more drugs) to be accurately divided in halves with regard to the dose, even if the tablet does not break into equal halves by mass.

The current invention describes a tablet shape adapted for separating one vertically disposed segment from another.

In the large field of immediate release pharmaceuticals, the relative dimensions of the tablets in accordance with the subject invention are novel as applied to immediate release dosage forms. Commercially, the only product that as produced is taller than it is wide is Concerta®, which is a three-segment tablet, two of which segments are devoted to controlled release of the active drug, methylphenidate. Concerta utilizes the OROS® system, which utilizes the taller-than-wide geometry to provide a layered tablet configuration to impart controlled release characteristics. The manufacturer's directions for the use of Concerta specify that the tablets should never be broken. Except for Concerta, tablets, including those involving layers vertically disposed one on the other, have been produced wider than they are tall.

A tablet press manufacturer, Korsch AG of Germany, has developed a tablet press (the TRP 900) that can produce up to five vertically disposed layers. It has been utilized to produce taller-than-wide five-layer tablets having no active drugs therein and has also been used to manufacture Concerta.

SUMMARY OF THE INVENTION

The subject invention relates to a segmented immediate-release tablet comprising at least three different compositions configured to form at least three different segments of a single dosage form, A preferred embodiment comprises a layered tablet having three segments—a top end segment, an inner or middle segment, and bottom end segment—each segment comprising a different composition. In this three-segment embodiment, the top end segment comprises a first immediate-release composition containing at least one active pharmaceutical ingredient, and the bottom end segment comprises a second immediate-release composition that also contains at least one active pharmaceutical ingredient. Preferably, at least one of the active pharmaceutical ingredients in the top end segment is different than at least one active pharmaceutical ingredient in the bottom end segment. The middle segment contains a third composition, different than either of the compositions of the top and bottom end segments and, preferably, is substantially free of active pharmaceutical ingredient, that is, it comprises an inactive composition consisting essentially of excipients having immediate-release properties or characteristics (referred to herein as "immediate-release excipients").

This novel configuration for immediate release tablets can result in previously undisclosed advantages so that breaking of the tablet may more easily produce predictable, accurate quantities of active ingredient(s) in the broken portions of the tablet. In certain embodiments, tablets of the invention are also preferably scored in a novel manner. These novel scoring configurations include a score completely through the composition that forms the end of the tablet and which extends into the adjacent, overlying composition or segment. This score completely traverses the vertical dimension, or thickness, of the layered end composition and thereby forms two (or more, depending on the score pattern) unitary end segments from that single composition. In addition, a substantially vertically oriented score can be formed in an outer side face of the tablet.

In one embodiment, the invention comprises an immediate release compressed pharmaceutical tablet that has two or more (preferably at least three, and more preferably at least four) different segments, has a top and a bottom and has, in certain alternative embodiments, after compression is completed, a height that exceeds the width of said tablet.

The height of the compressed tablet is measured vertically from the top to the bottom of the fully compressed tablet as it is oriented in the tablet die. The width of the tablet is measured as the greatest horizontal dimension of the tablet at a location halfway between said top and said bottom of said tablet, except that when the horizontal (transverse) cross-section of said tablet is substantially rectangular, the width is defined by locating the two shorter sides of the perimeter of said horizontal cross-section, and measuring the length of a line that is at a right angle to said shorter sides. More specifically, the width of a tablet in accordance with the subject invention refers to the longest horizontal (transverse) dimension of a tablet having a circular or ovoid cross-section, as the tablet oriented in the tablet die. In determining the width of a tablet that is substantially rectangular in transverse cross-section, diagonal measurements are not taken through the horizontal aspect of the tablet; rather, if the perimeter of the horizontal aspect of the tablet is rectangular (and not square), then the width of the tablet: would be the greater of the two perimeter side measurements, and not the diagonal that is measured form opposite corners or calculated by the Pythagorean theorem and that uses said perimeter side measurements to calculate said diagonal. Similarly, tablets with a substantially rectangular vertical cross-sectional configuration have a height that is measured as a perimeter and not a diagonal measurement. When a vertical or horizontal cross-sectional configuration is not substantially rectangular, which includes triangles, rhombi, and hexagons, the greatest dimension through said cross-section represents said height or width.

The height (vertical dimension), width (horizontal dimension) and any other dimensions or orientations or terms relating to tablet dimensions and structure such as "transverse" and "tallness," "bottom," "top," "end," "middle," "side," "outer," "superior," "inferior," "lower," "upper,"

"vertical," and "horizontal" refer to a spatial orientation of said tablet as oriented in a tablet die in which compression occurs, i.e., the terms relate to the position of the tablet as it is oriented within the die after final compression but before removal or ejection from the die of a tablet press or tabletting machine. Where the tablet has "cupping" of the top and/or bottom surfaces resulting from a concave or convex surface of a tablet die or tablet punch as conventionally used in a tablet press, the height relates to the maximal vertical distance, which can occur in the middle of the top surface as if there were a plumb line vertically dropped to the middle of the bottom surface.

Tablets of the invention are preferably produced for commercial sale in a high-speed multi-layer tabletting machine. Tablets are produced using a punch and die system as typically employed with said tabletting machine. Granulations enter the tablet die one on top of another, so that said granulations are said to be vertically disposed to each other. Layers and segments formed from vertically disposed granulations are considered to be vertically disposed, as well. The height ("tallness") of a tablet is measured as the vertical distance between the lowest part of the first granulation to enter the die (forming the bottom layer(s) or segment(s)) to the highest part of the last granulation to enter the die (forming the top layer(s) or segment).

Preferred tablets of the invention utilize an inactive segment, that is, a segment that comprises a composition that lacks or is substantially free of a pharmacologically effective dose of a drug, providing a discrete breaking unit that can serve as an inactive region or area for breaking through the tablet without substantially breaking through an active segment, and thereby providing an accurate partial dose of drug or drugs contained in the whole tablet, as desired. The inactive segment is preferably formed as a middle segment, between active segments which, in a three segmented tablet, form the bottom end segment (oriented below the inactive middle segment in the tablet die), and the top end segment (oriented above the middle inactive segment in the tablet die).

By convention herein, the term "contains a drug," when used to refer to a granulation, layer, or segment of a tablet, said granulation, layer or segment, or a plurality thereof, has within it a pharmacologically effective dose of an active pharmaceutical ingredient, or drug. The term "contain a drug or drugs" when used to refer to a granulation, layer, or segment means that said granulation, layer or segment, or a plurality thereof may contain either a single drug or a specific ratio of a plurality of drugs. A segment formed from a composition containing one or more drugs may be referred to as an "active segment" or "active composition" forming the segment.

A layer or segment, is said to "lack a drug or drugs" or to be "substantially free of a drug or drugs" or is an "inactive" layer or segment when the layer or segment is formed from a composition that either contains no drug or contains an undetectable or pharmacologically ineffective amount of a drug, by design or as a result of inadvertent intermixing or carryover during manufacture. For example, a composition containing only pharmaceutical excipients and is prepared as a substantially drug-free composition that, by being formed into a layer or segment of a subject tablet, then contains small amounts of drug resulting from intermixing or carryover from an adjacent active drug-containing composition, is considered to be substantially free of drug and an "inactive" layer or segment for purposes of the subject invention. Parts of speech, such as "contain," "contains," "containing," and "lacking" in relation to the above two paragraphs also are terms of art with otherwise the same meanings to those described therein.

A first preferred embodiment of the subject invention concerns a compressed, immediate-release pharmaceutical tablet containing a therapeutic dose of two or more active pharmaceutical ingredients. The tablet consists essentially of:

a first composition forming a bottom layered segment or a plurality of compositionally substantially identical segments forming an exposed bottom end surface of the tablet, said segment or segments having a contacting face located opposite and superior to the exposed bottom end surface of the tablet, said first composition consisting essentially of excipients having immediate-release characteristics anti a pharmaceutically effective dose of at least one active pharmaceutical ingredient;

a second composition forming a top layered segment forming an exposed top end surface of the tablet, said segment having a lower contacting face opposite and interior to the exposed top end surface, said second composition consisting essentially of excipients having immediate-release characteristics and a pharmaceutically effective dose of at least one active pharmaceutical ingredient, wherein, said first and second compositions are pharmaceutically compatible with one another and have at least one different active pharmaceutical ingredient;

a third composition consisting essentially of excipients having immediate-release characteristics and being substantially free of active pharmaceutical ingredient, said composition forming a middle layered segment having a lower contacting face in contact with the bottom end segment or segments, an exposed outer side surface, and an upper contacting face in contact with the top end segment, said middle segment having, after compression, an effective height of at least 2 mm, wherein the effective height is the vertical distance between a highest point of the bottom end segment or segments and a lowest point of said top end segment, said middle segment having a height or exposed side surface of at least 3 mm, said height of the middle segment being a vertical distance between the upper and lower contacting faces of the middle segment; and optionally, an immediate-release coating substantially free of active pharmaceutical ingredient.

The terms "bottom," "top," "end," "middle," "side," "outer," "superior," "inferior," "lower," "upper," "vertical," and "horizontal" used hereinabove and throughout this disclosure refer to a spatial orientation of the tablet as it is oriented in a tablet die in which compression occurs, before ejection of the final compressed tablet form the die.

A second preferred embodiment of the subject invention concerns taller-than-wide compressed, immediate-release tablet. A tablet according to this embodiment contains a therapeutic dose of two or more active pharmaceutical ingredients, has a height greater than width, (the height being measured vertically from the top to the bottom of said compressed tablet as oriented in the tablet die in which tablet formation occurs; and the width being measured as the greatest horizontal dimension of the tablet at half the height dimension, except that when the horizontal cross-section of said tablet is substantially rectangular, the width is the length of the long axis of said rectangle). The tablet of this second preferred embodiment consists essentially of:

a first composition forming a bottom layered segment or a plurality of compositionally substantially identical segments forming an exposed bottom end surface of the tablet, said segment or segments having an exposed outer side surface and a contacting face located opposite and superior to the exposed bottom end surface of the tablet, said first composition consisting essentially of excipients having immediate-release characteristics and a pharmaceutically effective dose of at least one active pharmaceutical ingredient;

a second composition forming a top layered segment forming an exposed top end surface of the tablet, said segment having an exposed outer side surface and a lower contacting face opposite and inferior to the exposed top end surface, said second composition consisting essentially of excipients having immediate-release characteristics and a pharmaceutically effective dose of at least one active pharmaceutical ingredient, wherein, said first and second compositions are pharmaceutically incompatible with one another and have at least one different active pharmaceutical ingredient;

a third composition consisting essentially of excipients having immediate-release characteristics and being substantially free of active pharmaceutical ingredient, said composition forming a middle layered segment having a lower contacting face in contact with the bottom end segment or segments, an exposed outer side surface, and an upper contacting face in contact with the top end segment, said middle segment having, after compression, an effective height of at least 2 mm, wherein the effective height is a vertical distance between a highest point of the bottom end segment or segments and a lowest point of said top end segment, said middle segment having a height or exposed side surface of at least 3 mm, said height of the middle segment being a vertical distance between the upper and lower contacting faces of the middle segment; and an optional immediate-release coating substantially free of active pharmaceutical ingredient.

Yet another, or third, preferred embodiment of the subject invention concerns compressed, immediate-release pharmaceutical tablet containing incompatible active pharmaceutical ingredients and having a tablet width greater than the tablet height. As in other embodiments described herein, the tablet height of this embodiment is measured, after said compression has been completed, vertically from the top to the bottom of said tablet as it is oriented in the tablet die in which it is fully compressed, and the width is measured as the greatest horizontal dimension of the tablet located half the height dimension below the top aspect of the tablet, except that when the horizontal cross-section of said tablet is substantially rectangular, the width is defined as the long axis of the rectangle. The tablet comprises at least four segments, which consist essentially of:

a first layered composition consisting essentially of a pharmaceutical composition containing excipients having immediate-release characteristics and a pharmaceutically effective dose of at least one active pharmaceutical ingredient, said first layered composition forming a bottom end segment or a plurality of unitary bottom end segments, said bottom end segment or segments having a contacting face contacting a second segment and an exposed end surface forming a bottom end surface of the tablet;

a second layered composition consisting essentially of excipients having immediate-release characteristics and being substantially flee of active pharmaceutical ingredient and forming a second segment having a first contacting face in contact with the bottom end segment or segments, an exposed side surface, and a second contacting face opposite the first contacting face and contacting a third segment, said second segment having, after compression, an effective height of at least 2 mm, wherein the effective height is a vertical distance between a highest point of the first segment and a lowest point of said third segment, said second segment having a height or exposed outer side surface of at least 3 mm, said height of the second segment being a vertical distance between the first and second contacting faces of the second segment, said second segment forming a breaking segment for optionally dividing said tablet through said third segment;

a third layered composition consisting essentially of excipients having immediate-release characteristics and a pharmaceutically effective dose of at least one active pharmaceutical ingredient, said composition being pharmaceutically incompatible with the first layered composition and wherein said first and third compositions have at least one different active pharmaceutical ingredient, said third composition forming the third segment having a first contacting face in contact with the second segment, an exposed outer side surface, and a second contacting face in contact with a top end segment;

a fourth layered composition consisting essentially of a pharmaceutical composition containing excipients having immediate-release characteristics and being substantially free of active pharmaceutical ingredient, said fourth layered composition forming a top end segment having a first contacting face contacting the third segment and all exposed end surface forming a top end surface of the tablet;

a substantially vertically oriented bisecting score in or on a side face and traversing at least two segments of the tablet, said vertically oriented score being provided for assisting a person to break the tablet at a desired break region when a half dose of all active ingredients is desired. A substantially vertically oriented score can, additionally or alternatively, be provided in an end surface of a top or bottom end segment, A substantially vertically oriented score in the bottom end composition can extend completely through that composition and into the middle segment, thereby creating a plurality of unitary segments from that bottom composition. These substantially vertically oriented scores, whether in or on a side surface or in or on an end surface of the tablet can be provided during a compression step in the manufacture of the tablet by providing a tablet die or punch comprising substantially vertically oriented embossing.

Thus, a preferred tablet of the subject invention comprises two different active compositions layered to form discrete segments of a tablet, preferably forming at least one active end segment, and in certain embodiments forming two active end segments, one at each end of a three-segment tablet. An inactive composition forms a third, discrete middle layer or segment and is positioned between those active segments (i.e., above the bottom end segment and below the top end segment in the tablet die). The inactive segment positioned between the active end segments can therefore serve as a discrete breaking unit or region or segment, providing an advantage of allowing a person to easily and accurately separate the active segments from one another, thereby dividing the dose contained within the whole tablet, without breaking any substantial part of, or losing any substantial amount of active ingredient from, either end segment. This advantage can ensure that the amount of drug contained within each active end segment in the whole tablet is substantially the same even after the tablet is broken into tablettes.

A tablet comprising four or more segments preferably includes at least one active end segment (or a plurality of unitary end segments), an inactive segment between and separating the active end segment(s) from a second active segment which is not an end segment, and further includes an inactive end segment. Though two or more different inactive compositions, or compositions that are substantially free of active pharmaceutical ingredient, could be used in a tablet of the subject invention, it may be preferred to use the same inactive composition in all inactive layers and segments of the tablet. All segment compositions of a tablet of the subject invention exhibit immediate-release characteristics. It is further preferred that the separating inactive segment disposed between the active segments is formed as a compound segment, using two consecutive rills of the same inactive composition. The separating inactive segment advantageously can form the discrete breaking unit or region or segment as in the three segment tablet described above.

The inactive end segment can provide an advantage of separating the two actives as disposed in the final product. This separation can also be advantageous to the tabletting process, where the manufacture of the tablets utilizes a rotating die table with a multi-layer tablet press. Such separation can be advantageous where the active pharmaceutical ingredients, or the compositions containing those active ingredients, are pharmaceutically incompatible, that is, either chemically or physically incompatible with one another. For example, stability of the two pharmaceutically incompatible APIs or compositions can be maintained by separating those APIs or compositions by at least one inactive composition that is pharmaceutically compatible with both APIs and compositions with which it comes into contact or is positioned proximate to in the rotating table of the tablet press. As would be recognized by persons of ordinary skill in the pharmaceutical arts, the term "incompatible" in reference to the APIs or the compositions containing them refers to two or more APIs or compositions which, when in contact or in close proximity to one another, may result in a detrimental effect to the chemical or physical stability of at least one of those APIs or compositions. For example, when two incompatible API is are mixed together in a compressed tablet, the chemical or physical stability of one or both of those APIs may be affected such that more rapid degradation or inactivation of the API can occur, e.g., degradation of an API may occur to a greater degree or more rapidly than if no other API or incompatible API were present. The degradation or inactivation can result from a chemical or physical property of one API, such as pH, chemical reactivity, hygroscopicity, or the like, negatively affecting another API contained in the same tablet.

Further, the preferred embodiments of the tablets according to the subject invention can include all immediate-release, substantially drug-free coating. The optional coating composition preferably comprises pharmaceutically acceptable ingredients that, when applied to the outside of the tablet, has substantially no effect on release kinetics of active drug from the tablet or tablette, and thus is referred to an "immediate-release" coating. In one preferred embodiment, the coating composition is a water-soluble composition comprising a sugar or starch (e.g., a saccharose), or a water-soluble polymeric composition (e.g., a low molecular weight hydroxypropyl methylcellulose or polyvinylpyrrolidone) or comprises other pharmaceutically acceptable excipients that are conventionally used as coatings for immediate-release tablets.

A tablet of the subject invention can further contain one or more guides for tablet breaking, such as a score, or other separation marks or indicia, such as printed indicia, or a perforation. These separation marks can be placed on or in a side or end surface of the compressed tablet. For purposes of the subject invention, a side of a tablet is an external part of the compressed tablet that has a vertical part substantially parallel to the theoretical vertical axis of the tablet. In an uncoated tablet, a side is in contact with the inner wall or face of the tablet die in which said tablet is compressed. The tablet in accordance with all embodiments described herein, can comprise a substantially horizontal score oriented in a side of a tablet, transverse to a vertical axis of the tablet. One preferred embodiment of a tablet in accordance with the subject invention includes a score oriented horizontally in reference to the longitudinal or vertical axis (height) of the tablet, and which is placed in the middle inactive segment of a three segmented tablet. Substantially horizontally oriented scores are preferably provided in a side surface of any segment of the tablet, are more preferably provided in a side surface of a middle segment (not an end segment), and are most preferably provided in a side surface of a middle, inactive segment. In addition, or in an alternative preferred embodiment of a compressed, immediate release tablet of the subject invention, a segment of the subject tablet can comprise printed indicia forming a mark or guide or the like to indicate or suggest a breaking region or area. The printed indicia is preferably formed as a line or other like marking oriented substantially horizontally on an exposed side of the middle segment such that a plane passing through said printed indicia substantially bisects the tablet or middle segment. It would be understood that a tablet of the subject invention may include a score and printed indicia on the same or oil different segments.

It would be understood that a substantially horizontal score cannot be readily formed during manufacture of the tablet using conventional process or conventional tablet press and is preferably formed in a separate post-compression step by removal of material from the side of the formed tablet. Substantially horizontally oriented scores are preferably formed after tablet compression has been completed because substantially horizontally oriented embossings can impede ejection of the tablet from the die. Such post-tablet scoring can be achieved by removal of material from the scored area using a cutting device or instrument, such as a blade, rasp or file, laser, or the like, as would be readily understood by persons of ordinary skill in the art. Preferably, the horizontal score is oriented such that a plane that would pass through said score is about halfway between the highest and lowest parts of said tablet, i.e. bisecting the tablet or middle segment. Alternately, the score can be positioned about equidistant from the highest point of a bottom segment and the lowest point of said top segment, i.e., bisecting the middle segment midway along its height, or its effective height.

A substantially horizontal separation mark or score can advantageously guide a user to break the tablet at the approximate position of the separation mark or score. Accordingly, a horizontal side score formed in a middle inactive segment can facilitate a user of the tablet to break the tablet only through one segment, e.g., the middle inactive segment, to avoid breaking through any part of an active segment. This can be advantageous for dividing the tablet into two discrete tablettes, each containing only one active ingredient. Preferably, the substantially horizontal score is oriented such that a plane that would pass through the score is about halfway between a highest and lowest point of said tablet. This scoring configuration provides a separation mark that substantially bisects the height of the tablet. Alternatively, the separation mark can be positioned to bisect the height or effective height of the middle segment (which may or may not be the same position as bisecting the height of the tablet), or approximately equidistant from a highest point of the bottom segment and a lowest point of the top segment.

The tablet may also comprise a substantially vertically oriented score in a side surface of at least one segment or in an end surface of a top or bottom end segment. Preferred tablets of the subject invention can also include a substantially vertically oriented score in a top surface of a top end composition or, preferably, a bottom surface of a bottom end composition, extending through the top or bottom end composition and into the middle segment, thereby forming two or more unitary end segments from that end composition. The number of unitary segments formed in the end composition can vary and depends on the configuration of the embossing on the tablet die or punch. For example, an "X"-shaped or "cross" configuration of the embossing can provide four unitary segments by quadrisecting end composition. Bisected, trisected, and pentasected end compositions are also contemplated for the subject invention and are limited only by the embossing configurations available in the tablet dies or punches. Alternatively, these and other simple or complex scoring patterns can be achieved by removing material to form a score after the final tablet has been formed.

The compressed pharmaceutical tablets can include one or more active pharmaceutical ingredient (API) suitable for preparation into a compressible composition or formulated with a pharmaceutically acceptable carrier or carriers such that the formulation can be compressed into tablet form. Preferably, the API is a drug that is approved or is approvable for commercial sale in the United States, such as a calcium channel blocker (CCB), angiotensin converting enzyme (ACE) inhibitor, an angiotensin receptor blocker (ARB), a thiazide diuretic, or a beta blocker (BB). Known CCBs include, for example, amlodipine, verapamil, diltiazem, nisoldipine, felodipine, isradipine, lacidipine, lercanidipine, nicardipine, manidipine, or nifedipine. Known ACE inhibitors include, e.g., captopril, enalapril, lisinopril, ramipril, trandolapril, quinapril, perindopril, moexipril, benazepril, or fosinopril. Known thiazide diuretics include, for example, chlorthalidone, hydrochlorothiazide and/or chlorothiazide.

In one preferred embodiment of the subject invention, the tablet comprises at least one CCB in one end segment, and at least one ACE inhibitor in the other end segment. A more preferred tablet of the subject invention comprises amlodipine as the active pharmaceutical ingredient in one end segment, and benazapril as the active pharmaceutical ingredient in the other end segment. In another preferred embodiment of a tablet having four segments, a bottom end segment contains an active pharmaceutical ingredient selected from either amlodipine or benazapril, a second segment immediately superior to the bottom segment is formed from one or more layers of an inactive composition, a third segment immediately superior to the second segment is formed from an active composition containing either amlodipine or benazapril (whichever is different than is contained in the bottom segment) and, finally, an inactive top end segment. This embodiment can It would be understood that the use of any one of the active pharmaceutical ingredients includes the use of its pharmaceutically acceptable salt, derivative, isomer, polymorph, prodrug, or a metabolite thereof.

Taller-than-wide tablets of the invention are shaped to be more easily broken through the tablet's theoretical vertical axis (i.e., in a horizontal direction) than conventional, currently-manufactured tablets having a "wider than tall" configuration. Many preferred uses of tablets of the invention are to break through a middle, substantially inactive segment of the tablet without breaking through any segment above or below said middle segment. However, the subject invention also includes tablets that are "wider-than-tall." Preferably, these wider-than-tall tablets of the subject invention include vertical scoring in or on a side of the tablet, or in or on the active, end compositions or segments which can facilitate breaking of the tablet scored end composition or segment. When these vertical scores are broken through first, the resulting tablette can effectively be a "taller-than-wide" tablette with active end tablette segments and an inactive middle tablette segment. A second break can then occur through the middle tablette segment, with the same advantage of no or minimal further breakage of either end tablette segment.

It is a primary object of the invention to provide an immediate release pharmaceutical tablet that may be easily broken to provide a partial dose of a drug or drugs that is contained in the whole tablet or a resulting tablette.

It is also an object of the invention to provide an immediate release pharmaceutical tablet having at least three segments, one of which is an interposed segment which is adapted to be broken through in such a manner as to keep the segments between which it is interposed and that contain pharmacologically effective quantities of a drug or drugs substantially intact if said tablet is broken through said interposed segment.

These and other objects of the invention will become apparent from the present application.

BRIEF DESCRIPTION OF THE SEVERAL VIEWS OF THE DRAWINGS

FIGS. 7A and 7B depict a front view of two tablettes, respectively, formed by breaking through the horizontal score of the tablet shown in. FIG. 5.

DETAILED DESCRIPTION OF THE INVENTION

Figure 1B:
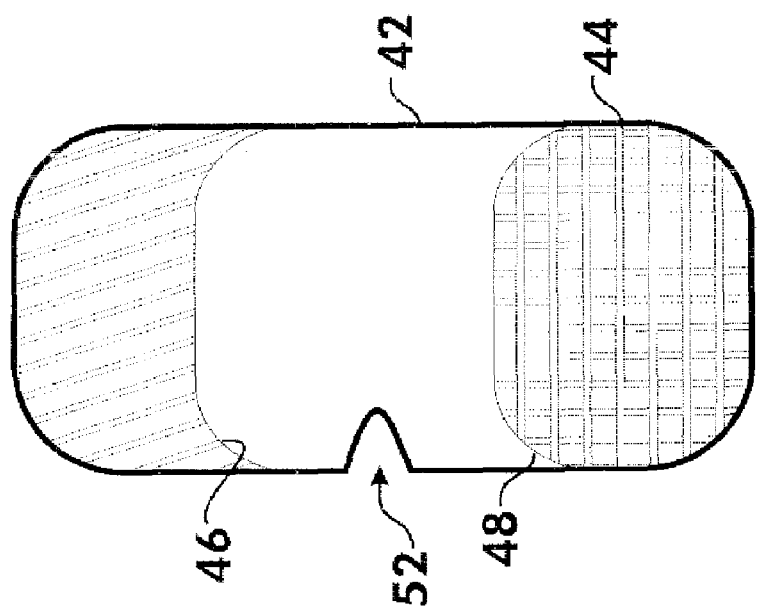
FIG. 1B is a cross-sectional view of the tablet of FIG. 1A, looking at the side of the tablet where the score ends.

Tablets of the invention are preferably those compressed in a tablet press. For commercial use, a high-speed three (3)- or five (5)-station press produced by Korsch AG (such as the TRP 700/900 tablet presses) may be utilized. Remington's Pharmaceutical Sciences 20th Ed., Mack Publishing Co., Easton, Pa. (2000), Chapter 45, which is incorporated by reference, describes the various techniques utilized in making compressed tablets, and pharmaceutically acceptable excipients that can be used in a formulation with active pharmaceutical ingredients to form immediate-release compressed tablets of the subject invention. The tablets of the invention are primarily intended for oral administration but they may also be used for other applications. Tablets of the invention are preferably not formed using an adhesive substance, such as cement, glue, other adhesive, or the like to adjoin segments or discrete units.

If an optional coating is provided on the tablets of the invention, such coating preferably comprises a water-soluble coating, e.g., a water-soluble polymeric coating comprising, for example, a water soluble cellulosic polymer, polyvinylpyrrolidone (PVP), or the like, for the well known purposes of aiding in manufacture or handling of the tablet (e.g., to decrease susceptibility to chipping during manufacture or shipping, to improve aesthetics of the tablet, to protect against exposure to light, to improve mouth-feel or to facilitate swallowing of the tablet). A coating provided on an immediate-release tablet of the subject invention preferably does not affect the immediate-release characteristics of the tablet, and preferably is substantially free of active pharmaceutical ingredient. Such coating in accordance with the subject invention is not for the purpose of altering the release kinetics of any active ingredient present in the tablet, such as a swellable or erodible coating used to slow the release of drug from a tablet after ingestion. The coating may contain a color or coloring agent.

The tablets of the invention comprise at least two compositionally different segments, e.g., one active composition disposed to form two different (top and bottom) segments, and one inactive composition disposed to form the middle segment. Thus, two different compositions are used and form three discrete segments in a tablet of the subject invention.

A segment represents the entirety of a contiguous, substantially homogeneous part of a tablet or tablette (see below) of the invention. If two or more consecutive granulations entering the die are substantially identical, then when compressed, they will form one segment. Such a segment is a sub-type of segment that may be referred to specifically as a compound segment. If, however, two substantially non-identical granulations (such as those containing different active drugs, the same active drugs in different ratios, different excipients or different ratios of similar excipients, or different salts of the same active drug) were compressed onto each other, they would comprise two segments. Granulations comprising the same active drug in the same concentration relative to excipients but with dissimilar excipients would comprise two segments if one granulation were compressed onto another.

A layer is produced by introducing an amount of an individual granulation into a tablet die to fill at least a part of the die. A layer is considered to be present whether it is the form of an un-tamped, tamped or fully compressed granulation.

In many of the most preferred tablets of the invention, a layer, (and the granulation from which it is derived), will not need to be placed on top of or below (e.g., adjoining, or contiguous with) a substantially identical layer (or granulation). In such a case, one layer will give rise to the sub-type of segment that is a simple segment. The use of the term "segment" allows a segment to be simple or compound.

Because the tablets of the invention have been adapted to be broken if and when desired, it has proven useful to develop a term for the major fragments of said breaking. The inventors use the term "tablette" in this regard. An example of tablette formation is as follows. A standard single-scored, mono-layer, homogeneous pharmaceutical tablet is broken. Said breaking produces two major fragments, each of which is called a tablette, generally plus some chips and crumbling which are preferably minor in amount. In the segmented, layered tablets of the invention, to utilize the invention properly may make it advantageous to place a score transversely into a segment, such as an inner segment, as may be done with an instrument such as a file. Successfully breaking said tablet through said score will result in two tablettes, representing the two major fragments of the tablet and not including smaller fragments such as crumbs or chips. The accompanying diagrams help clarify the relationship of tablets to tablettes.

The terms "active agent," "drug," "active drug," "active pharmaceutical agent," "pharmacologically active agent" are interchangeable and include, without limitation, prescription and non-prescription pharmaceutical compounds, as well as pharmacologically effective doses of vitamins, cofactors, and the like. Substances such as foodstuffs, vitamins in "recommended daily allow" quantities, and the like are not considered to be "drugs" herein.

The term "undetectable amount" means that using conventional analytical techniques such as high performance liquid chromatography (HPLC), nuclear magnetic resonance imaging (NMRI), and the like, the presence of an active compound can not be identified. The term "pharmacologically ineffective amount" means an amount of a drug or drugs having no measurable pharmacological effect. Due to the conditions under which high speed automated tabletting equipment are operated, mixing of different granulations may occur during tablet formation which may cause material such as drug substance present in one granulation to appear in a layer or segment where it was not intended to be placed.

The terms "inactive segment" or "substantially inactive segment" or "relatively inactive segment" refers to a segment that either contains an undetectable amount of any drug or contains a diminished concentration of any pharmacologically effective drug or drugs contained in another segment or segments or is formed from a composition that is substantially free of active drug in its manufacture prior to its incorporation into a tablet of the subject invention.

The term "immediate-release" refers to the release of drug from a composition, where the drug is substantially completely released within a time period of about 1 hour or less and, preferably, about 30 minutes or less. An immediate-release dose of drug applied as a coating on the surface of a dosage form, as used herein, refers to a dose of a drug prepared in a suitable pharmaceutically acceptable carrier to form a coating solution that will dissolve rapidly upon administration to thereby provide an immediate-release dose of drug. As is known in the art, such immediate-release drug overcoats may contain the same or a different drug or drugs as is contained within the underlying dosage form.

As used herein, such terms as "horizontal" ("transverse") and "vertical" when used in relation to a tablet, are based on the spatial orientation of the tablet as, and after, it is produced in a die, but before it is removed or ejected from the die. Thus, the top layer (segment) of the tablet is considered to be above the inner and bottom layers (segments). The layers and segments of the tablet are considered to be vertically disposed with regard to each other, as granulations enter and form layers vertically. An "inner" segment is a "middle segment" and the terms are used interchangeably herein.

The height of a tablet represents the vertical distance from the lowest part of the tablet to the level of the highest part. There are two transverse dimensions, measured by taking a cross-section of the tablet through its widest part. Unless the cross-sectional configuration of the tablet is circular or square (excluding beveling or cupping at the periphery of an otherwise square cross-sectional shape), then there are at least two different transverse dimensions. The greater of said two transverse dimensions is called the width, and the lesser is called the depth. Tablets of the invention comprise at least two segments, have release characteristics that are immediate release (i.e., there are no controlled-release or "drug delivery" coatings, additives, or characteristics), and have a height that exceed the width.

As an example of a preferred method of manufacture of a tablet in accordance with the subject invention, first, a granulation containing a pharmacologically effective dose of a drug enters the die and is, optionally, tamped. Second, a granulation lacking a drug (an "inactive granulation") enters the die and is optionally tamped. Optionally, a second and perhaps a third identical granulation lacking active drug also enters the die and is tamped. The inactive granulation(s) create(s) a breaking region or area within the tablet—a part of the tablet that can be identified and broken through so that a part of the tablet containing a significant concentration of drug is not broken through. Last, a second granulation containing a pharmacologically effective quantity of a drug enters the die, is optionally tamped, and then final compression to form a compressed tablet occurs. In the preferred embodiment of the invention, this second granulation is compositionally substantially identical to the first active granulation. While one or all segments may individually have a width greater than height, the tablet as a whole preferably has a height that exceeds its width.

Often, to aid identification of the inactive segment, the top and bottom segments can be of a different color than the middle inactive segment; this is a preferred embodiment. Other markings in or on the tablet may also aid identification; or, it may be advantageous not to make such identification of the different segments obvious.

Subsequent to tablet formation, optionally a score may be placed in the side of said tablet, preferably transversely. Alternatively, after tablet formation, a printed line or other forms of indicia such as dotted lines, symbols or perforations may be placed on or in the surface of the tablet, all of which serve the purpose of allowing identification of said tablet's desired breaking region from the standpoint of effecting accurate separation of the parts of a tablet containing isolated doses of drug.

A horizontal score as described herein for tablets of the subject invention cannot be produced by conventional or commercial tablet manufacturing techniques because to do so would require a corresponding horizontal "shelf" or "embossing" in the die that would allow tablet formation but would prevent ejection of the formed tablet from the die. Such a score may, however, be produced by other means, such as by use of a file manually or by a high-speed manufacturing process. Various methods of applying indicia such as pharmaceutically acceptable inks and banding materials are well known and may be applied to the side of the tablet, such as to locate a region of potentially desired tablet breaking, such as through a relatively inactive middle segment which is interposed (i.e., located) between two segments.

The depth of a score may be from about 0.5 mm to about 3 mm but, preferably, should not exceed from about 40-50% of the thickness (or width) of the tablet. The score can include interrupted, incomplete, or non-contiguous scoring marks. The length of the printed indicia mark is not limited and in the case of a rounded tablet may include 30° to 180° of are or more preferably from 60 to 120° of arc; in the case of a rectangular, trapezoidal etc. tablet, the score may include from about 10% to 50% percent of the perimeter of the tablet measured at the point where the printed indicia mark is placed.

A score also may be provided within a top segment or a bottom segment, oriented horizontally or vertically, in the tablets of the invention.

Suitable dimensions for tablets according to the invention are; height: 6 to 24 mm; preferably 10 to 18 mm and more preferably from 10 to 14 mm; width (at the widest dimension of the horizontal axis): 2 to 16 mm; preferably 3 to 10 mm and more preferably 4 to 8 mm. Without limitation, the dimensions of the tablet may be optimal if the ratio of the height to the width is between about 1.5:1 to about 3:1. None of these dimensions are limiting, and they are presented regarding use in adult humans. The invention may be useful in animals of different size, in which case preferred dimensions may be very different from those provided immediately above, but could be adjusted or modified by a person of ordinary skill in the art guided by or using the disclosure herein.

Numerous other tablet structures may be created, some of which are further delineated below. Various advantages in the treatment of human patients and other animals in need are created by tablets of the shape described.

Tablets of the invention are most preferably formed in a high-speed tablet press. In a typical manufacturing procedure, two or more different granulations are separately fed into a die, utilizing different filling stations. Wet granulations are often preferred to limit transfer of material from one granulation to another. Direct compression of powder is also a preferred manufacturing technique.

Benefits of the invention include the utilization preferably of inactive granulations, and less preferably, segments with diminished concentration of a drug relative to another segment. Optimally but not necessarily the tablet is provided with a means of identifying an optimal breaking region and of identifying one tablette from another after tablet breaking, an important benefit if the tablettes contain different types or quantities of a drug or drugs.

Because of the novelty of the tablets, it is necessary to describe the top, bottom, sides, etc. of the tablet. It has been found best to describe the tablet with regard to such terms based on said tablet's formation and location in the die in which said tablet is formed.

The bottom segment of a tablet contains the first granulation into the die. The top segment of a tablet contains the last granulation to enter the die. A "side" of the tablet refers to that external part of said tablet in contact with the internal vertical face or aspect of the tablet die in which said tablet is produced. Typically, sides of the tablets of the invention are vertically oriented, in contrast to the tops and bottoms of the invention. In the case of cupping and beveling of the top of the tablet, which may from time to time be extensive, the tablet's side is considered to also include the external part of the tablet that was in contact with the internal vertical face or aspect of the tablet die before a top punch formed said cupping, beveling, or the like.

If separate granulations were to be sequentially placed in a die horizontally (side-to-side) and not vertically as is currently the practice, then the tablets so produced would be within the scope of the present invention as the same product would be produced. When the tablet of FIG. 1, for example, is laid on a flat table, it will tend to lie lengthwise at right angles to the manner in which it is formed in the die (i.e., its longest axis would lie horizontally in relation to the tabletop), so that if the three segments were all different colors, then the segments would appear to be arranged not vertically (one on top of the other), but rather horizontally (side-to-side). For consistency of terminology, such segments nonetheless are considered herein to be disposed vertically on top of each other, because of the manner in which they were created.

One major advantage of the invention is that it optimizes optional tablet breaking. When force is applied to break a tablet, breaking of the tablet tends to more easily produce predictable quantities of active ingredient(s) in tablettes than "wider than tall" tablets with segments containing the same quantities of drugs. The tablet may be broken according to the invention either by applying force such as a cutting edge directly to the region to be broken through, or to outer segments, potentially in either case breaking through an inner segment.

Examples of specific embodiments of the invention are best described with reference to the drawings. Shaded areas represent segments derived from active granulations, i.e., those which contain a drug; clear (plain) areas represent segments derived from inactive granulations, i.e., those formulated with no active drug.

The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

"Front views" refer to a cross-sectional view of a tablet that has a theoretical geometric plane passed through the tablet relative to a side which is arbitrarily designated as the front. Figures labeled as "side view," which also have a corresponding "front view" are taken as a cross-section through the whole tablet from the right side of a front view i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view.

That plane is located half-way between the front and back surfaces of said tablet. The side views of FIGS. 1a-b and 2a-b are taken from a vertically-oriented plane that passes through the midpoint of the longer transverse dimension (i.e., the width), and thus are located at and perpendicular to the mid-point of the front view. Drawings are of tablets that have a rectangular but not square horizontal cross-section at the vertical mid-point of the tablet.

Segments containing pharmacologically active amounts of a drug or drugs are shown crosshatched; pharmacologically ineffective segments are shown plain (clear, without crosshatching or stippling). The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet ejection from the die. Dotted lines in the tablets depicted in the Figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the Figures imply no intention to limit the depth of any scores of the tablets of the invention. Horizontal dotted lines on the front views that represent the surface scores are schematic, and do not necessarily represent the full vertical extent of a score, printed mark, or the like.

Tablettes are depicted with broken surfaces, as indicated by a saw-tooth pattern. Such saw-tooth depiction is schematic and not intended to represent the actual pattern of breaking of a tablet (or tablette, which often leads to irregular edges even if said tablet is broken through a score.

Grasping and breaking said tablet is easier with the current, taller-than-wider design than would be the case under layered (segmented) tablets known to the art, in which breaking a tablet through one segment only, if feasible, would require "filleting" the tablet through its longest axis.

Figure 1A:
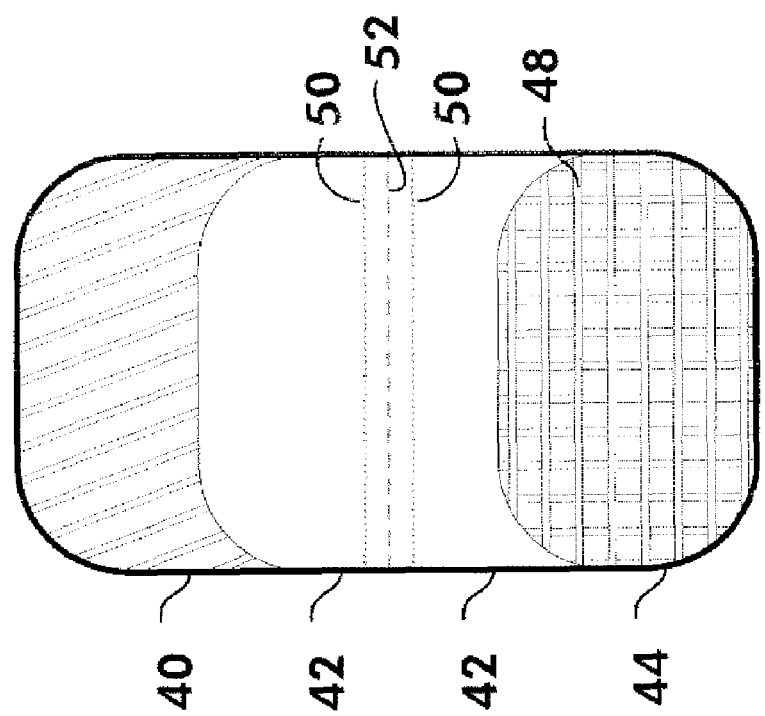
FIG. 1A depicts a cross-sectional front view illustrating a:n embodiment of a taller than wide tablet of the subject invention, looking towards the side of the tablet having a horizontal score formed in the middle segment.
Figure 2C:
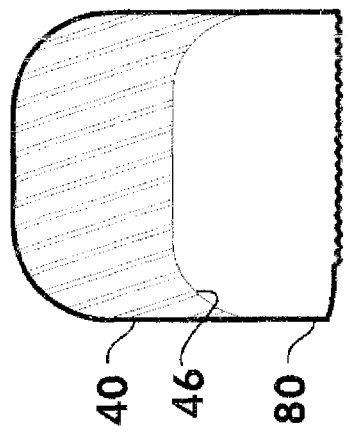
FIGS. 2 A-B and FIGS. 2 C-D depict tablets as shown in FIG. 1A and FIG. 1B, respectively, after those tablets have been broken through the horizontal score.
Figure 2D:
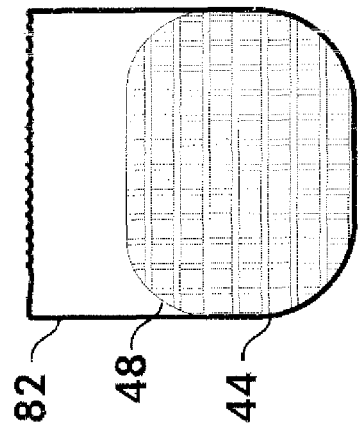
Figure 2A:
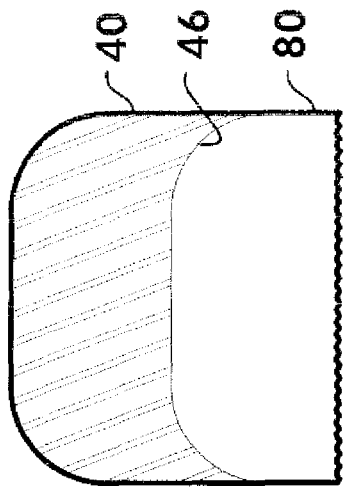
Figure 2B:
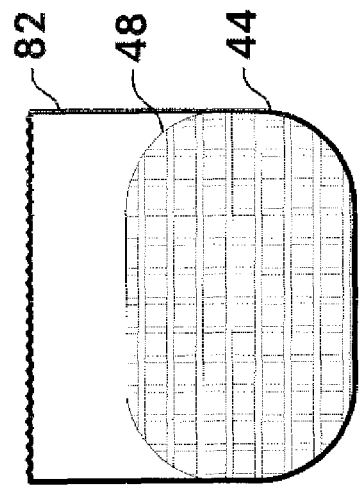

FIGS. 1A and 1B depict cross-sectional views of a three-segment tablet having an upper end segment 40 and a lower end segment 44. FIG. 1A depicts a cross-sectional front view illustrating an embodiment of a taller than wide tablet of the subject invention, looking towards the side of the tablet having a horizontal score formed in the middle segment. The lower segment 44 is compositionally substantially different than the upper segment 40. Both the upper segment 40 and lower segment 44 comprise a pharmaceutically effective amount of at least one active pharmaceutical ingredient. Middle (or liner) segment 42 comprises a composition that is substantially free of active ingredient, but may contain, as an artifact of the manufacturing process, trace amounts of drug present in either of segments 40 or 44. FIG. 1B is a cross-sectional view of the tablet of FIG. 1A, looking at the side of the tablet where the score ends. Interfaces 46 and 48 represent regions in which the upper part of the middle segment 42 and the lower part of middle segment 42 respectively adjoin upper segment 40 and lower segment 44. The curved interfaces of the adjoining segments result from the profile of the upper tablet punch which typically has a curved surface. Substantially horizontal score 52 is depicted in FIG. 1B, and is depicted as a reflected dotted line in FIG. 1A. Dotted lines 50 in FIG. 1A depict the faceted score 52 as reflected from the surface of the tablet (not shown), that does not penetrate half-way through the shorter transverse axis of the tablet.

FIGS. 2A-2D depict tablettes formed from breaking the tablet of FIGS. 1A and 1B through score 52. Middle segment 42 of FIG. 1A no longer exists as an intact segment. The upper tablette of FIGS. 2A and 2C contains a portion of segment 42 (shown as segment 80) that adjoins intact upper segment 40 and the tablette of FIGS. 2B and 2D contains a different, remaining portion of segment 42 (shown as segment 82) which adjoins intact lower segment 44.

Because of the taller-than-wide configuration of the tablet of FIGS. 1A and 1B, breaking through the substantially horizontally oriented score 52 placed in segment 42, for example manually dividing the tablet through the horizontally scored middle segment, is clearly easier than breaking the tablet through its vertical dimension, which is currently the practice with scored layered (segmented) tablets. The fact that no break is made in the upper end or lower end segments, or any other parts of the tablet containing, more than trace amounts of active drug, provides for exceptionally accurate breaking relative to the active drug or drugs contained in the whole tablet or any resulting tablette.

Figure 3:
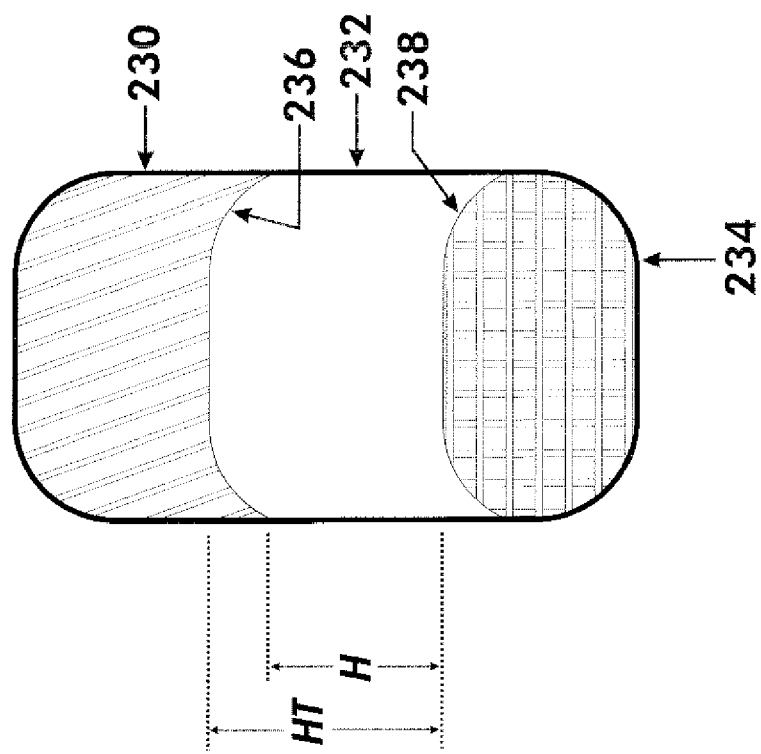
FIG. 3 depicts a front view illustrating a tablet according to an embodiment of the subject invention, where the tablet has three segments and further illustrates the measurement for height and effective height of the middle segment.

FIG. 3 is a cross-sectional front view of an unscored three-segment tablet, having a top segment 230 containing a drug, an inactive middle segment 232 (containing either no detectable drug, only trace amounts of drug, or at most a pharmacologically ineffective amount of a drug) and a bottom segment 234 which comprises a composition which is distinct from the composition of the upper segment. Typically, the upper and lower compositions differ by having at least one different active pharmaceutical ingredient contained therein. This embodiment of the tablet of the subject invention, as is the tablet of FIGS. 1A and 1B, is formed with a tablet punch having a curved profile which forms curved interfaces 236 and 238 as well as a curved top end surface of the tablet. The effective height of the middle segment is H which is less than the actual height HT of the middle segment due to the effect of the curved tablet punch. It is desired to break this type of a tablet only through that part of the middle segment within the effective height H to avoid breaking into the drug-containing top or bottom segment.

The above-described tablet contains three layers and three segments. One of the upper or lower active segments may contain amlodipine and the other segment may contain benazapril. It may be broken through the middle segment formed from the inactive composition, e.g., granulation. Said breaking, when confined solely to said middle segment, will create two tablettes, one substantially intact segment comprising amlodipine and a part of the middle segment, and another substantially intact segment comprising benazapril and the remaining part of the middle inactive segment. The advance on the art of tablet splitting is that maximal accuracy of dosing present in each tablette will be achieved, since any weight (or mass) difference between the two tablettes will be due to differences in the quantity of middle segment present, but said middle segment is expected to have little if any amlodipine or benazapril therein. Similarly, any loss of mass due to chipping or crumbling is expected to occur only in the substantially inactive middle segment.

Figure 4:
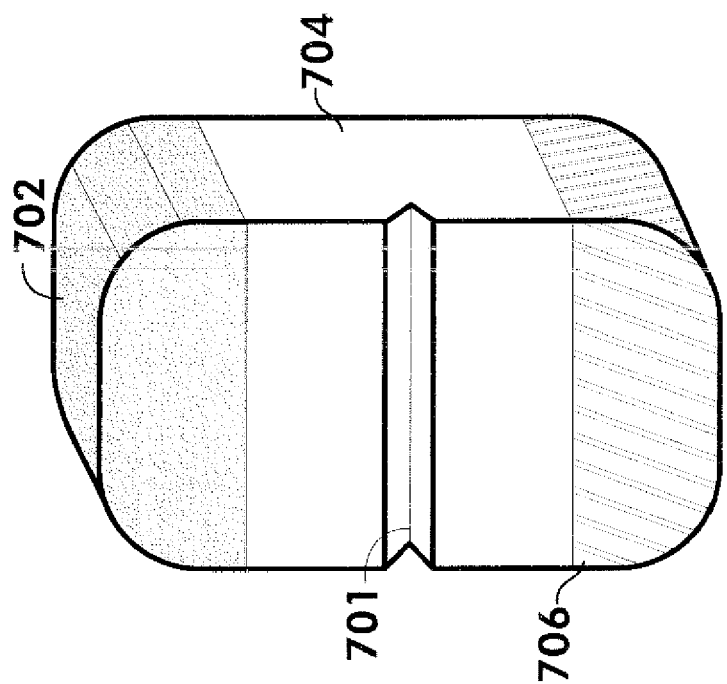
FIG. 4 depicts a perspective view of a tablet of the subject invention having three segments and a horizontal score in the middle segment.

FIG. 4 is a perspective view of a tablet of the invention which shows score 701 on a front surface of the middle inactive segment 704, a top active (drug-containing) segment 702, and a bottom active segment 706 which is compositionally substantially different from the top segment. When the tablet is broken through the score 701, the top segment and the bottom segment will each remain intact, but be contained tin separate tablettes. Segments 702 and 716 each contain a substantially different composition, each comprising at least one active pharmaceutical ingredient or drug. Typically, for tablets of the subject invention, the top and bottom end segment comprise compositions that each contain a single active pharmaceutical ingredient, and which are different from one another. For example, a tablet of the subject invention can have a top segment comprising an immediate-release composition containing drug A (plus excipients) and a bottom end segment comprising an immediate-release composition containing drug B (plus excipients).

However, it would be understood that compositionally different segments can contain the same drug, but will contain other different components or excipients, or an additional drug. For example, a tablet of the subject invention can have a top segment comprising an immediate-release composition containing drug A (plus excipients), and a bottom segment comprising an immediate-release composition also containing drug A (plus excipients) and also containing drug B. Thus, the compositions of the upper end segment and lower end segment, though containing one drug in common, will be considered to be compositionally different from one another.

Figure 5:
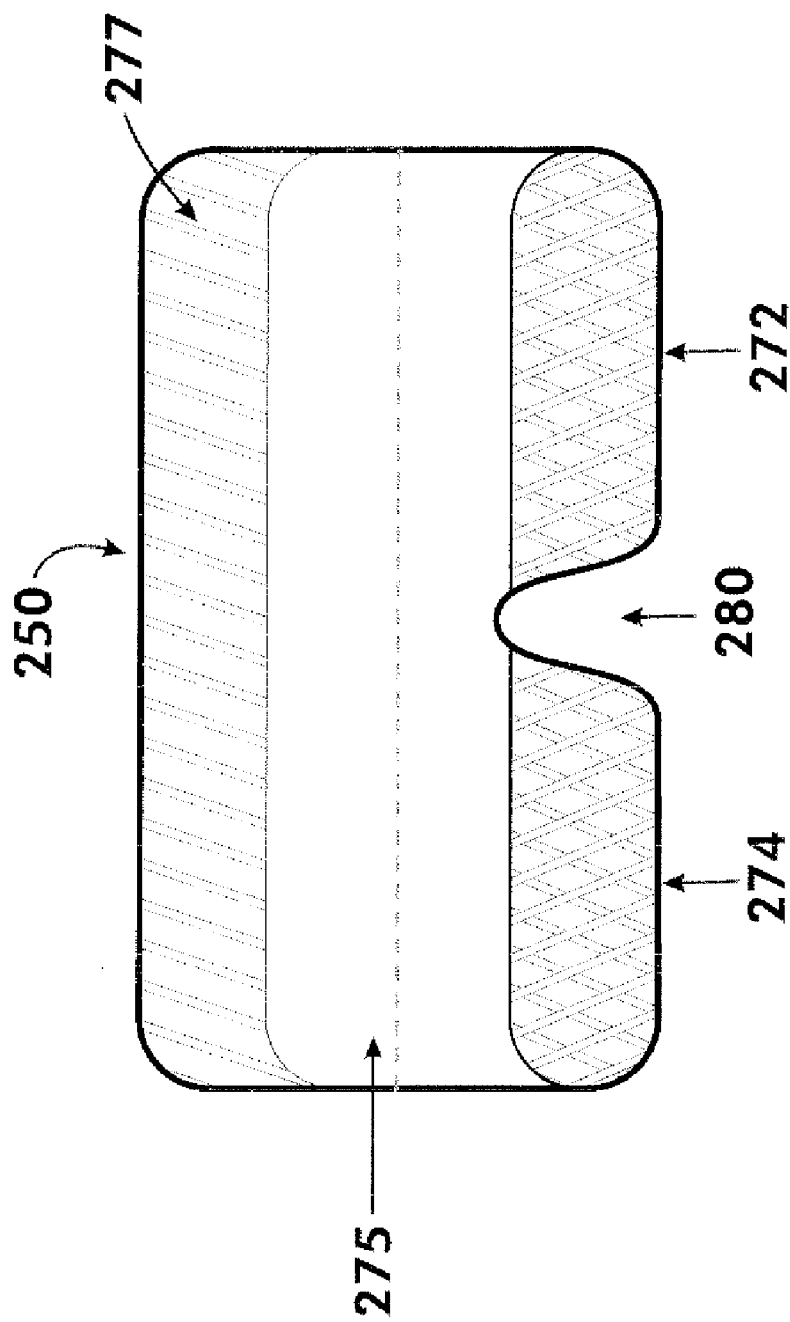
FIG. 5 is a cross-sectional front view of a four segment tablet with a vertical score formed in the bottom layered composition (forming two bottom end segments therefrom), the score extending through the bottom composition and into the middle segment, and a horizontal score in the middle segment (dotted line reflecting horizontal score formed in outer face of middle segment).

FIG. 5 is a cross-sectional front view of a tablet of the subject invention, depicting tablet 250 containing flour segments. Unitary segments 272 and 274, as with all unitary segments, are not contiguous with each other, but are formed by the same layer or layers and comprise the same composition. Score 280 extends or penetrates completely through the layer or layers forming unitary segments 274 and 272 and into inactive middle segment 275. Segment 275 is preferrably a compound segment formed from a plurality of layers of substantially compositionally identical inactive granulations added sequentially. Top segment 277 contains a therapeutic quantity of at least one drug and is compositionally different than the composition forming segment 274 and 272. Dotted line 12 reflects a surface score that runs transversely or substantially horizontally across the outer surface of middle inactive segment 275. A preferred horizontal dimension for the tablet of FIG. 5 is about 12-18 mm, but said dimension is not limited.

The tablet of FIG. 5 may be broken usefully in two ways. One way the tablet of FIG. 5 may be broken usefully is vertically, through score 280 in the direction of segments 275 and 277; such breaking would not utilize the score reflected by dotted line 12, but would give a dose of half of the drug found in segments 274 and 272, though may not give as precise halving for the drug found in segment 277, due to difficulties with breaking scored tablets as was documented hereinabove. Another way to successfully break tablet 250 of FIG. 5 is to break the tablet horizontally along the score reflected as score 12. Breaking through score 12 is preferably done after breaking the tablet into tablettes using score 280. Thus score 12 is preferably used to further divide a tablette containing segment 274 and about half of segment 277, or to further divide a tablette comprising segment 272 and about half of segment 277.

Figure 6B:
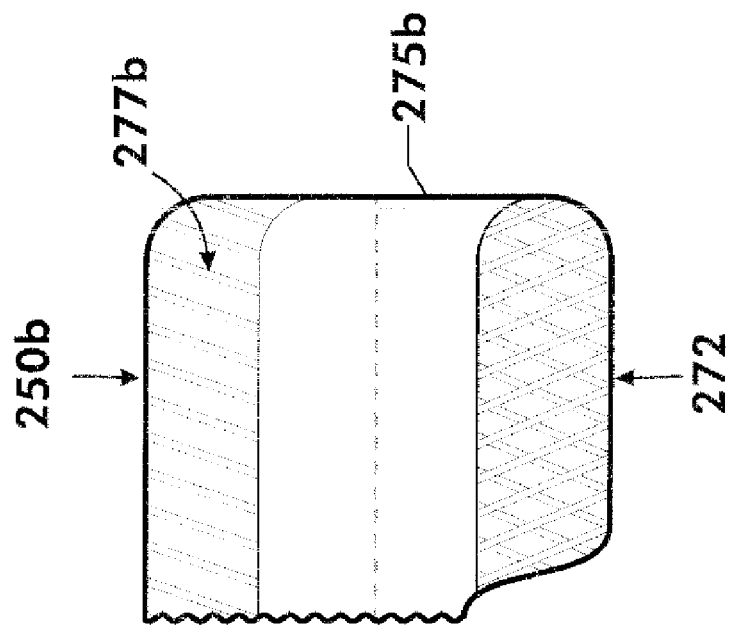
FIGS. 6A and 6B depict a front view of two tablettes, respectively, formed by breaking through the vertical score of the tablet shown in FIG. 5.
Figure 6A:
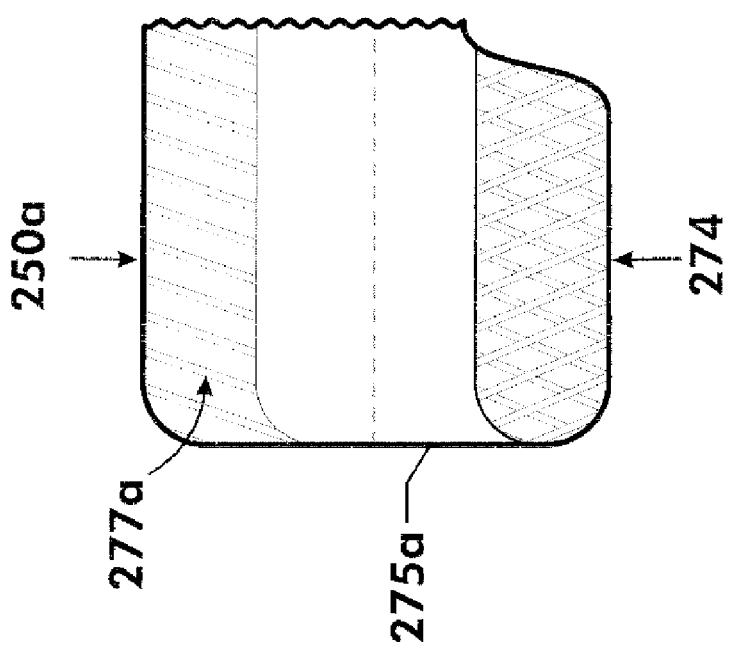

FIGS. 6A and 6B depict the two tablettes 250a and 250b created by breaking the tablet 250 of FIG. 5 vertically, at score 280 and through segments 275 and 277. In FIG. 6A, after segment 275 is broken through, segment 275a represents that part of segment 275 that adjoins intact segment 274, and in FIG. 6B, segment 275b represents that part of segment 275 that adjoins intact segment 272. Segment 274 in tablette 250a of FIG. 6A and segment 272 in tablette 250b of FIG. 6B advantageously have a mass substantially equivalent to one another.

Figure 7A:
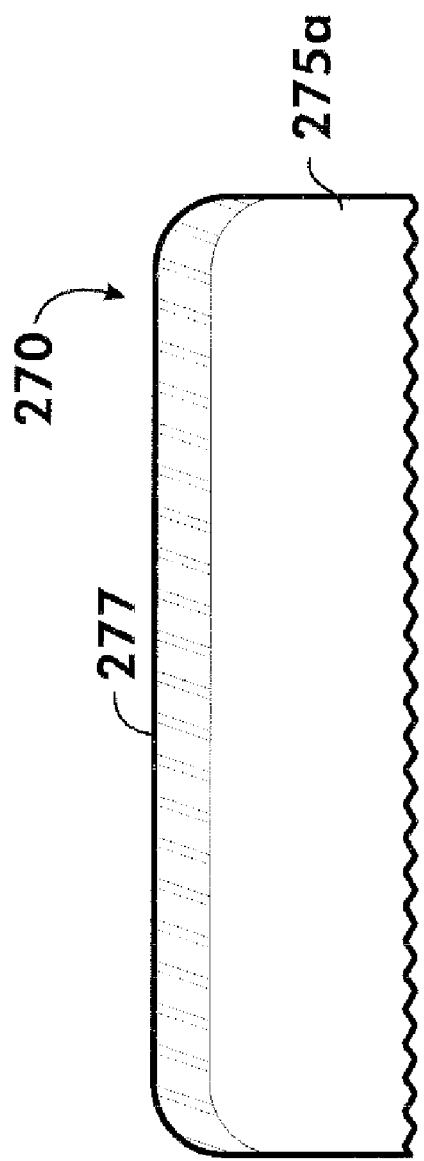
Figure 7B:
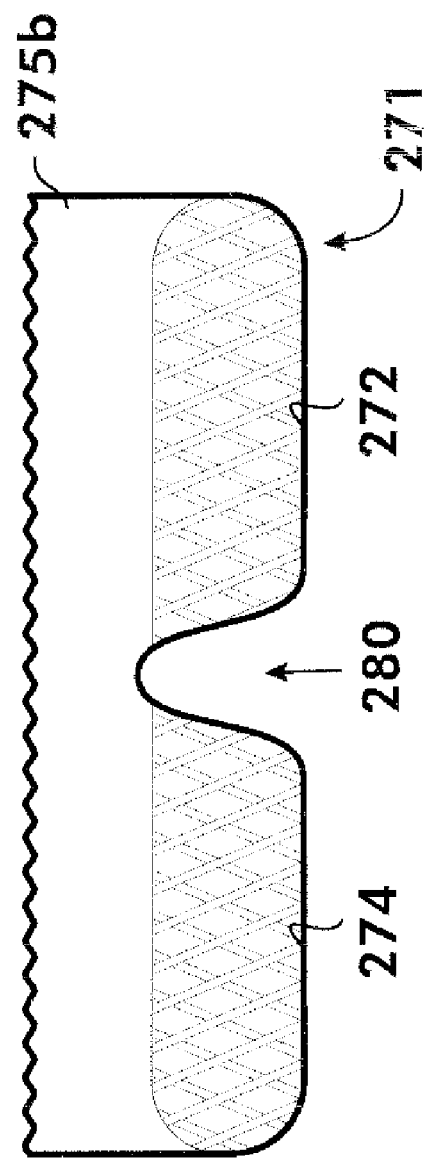

The result of another way of breaking said tablet is depicted in FIGS. 7A and 7b. FIG. 7a shows a tablette 270 comprising unbroken or intact segment 277 and a broken portion of FIG. 5 tablet segment 275 (the broken portion being designated as divided middle segment 275a). Tablette 270 can be formed from breaking the tablet 250 of FIG. 5 through the horizontal score reflected by dotted line 12. As with other tablettes depicted herein, it is not assumed that breaking is even, but the tablettes are depicted so that breaking is contained substantially within FIG. 5 tablet segment 275, that is a segment interposed between tipper segment 277 and lower segments 274 and 272 in the tablet 250 of FIG. 5. Tablette 270 of FIG. 7A demonstrates that segment 277 is intact, after breaking through the score 12. Segment 275a is formed by the broken part of therapeutically inactive segment 275 of the tablet of FIG. 5 that remains contiguous with segment 277. Tablette 271 of FIG. 7B depicts segments 274 and 272, as intact and unchanged from the tablet 250 of FIG. 5. Segment 275b is the part of FIG. 5 segment 275 that becomes part of the tablette 271 of FIG. 7B after breaking through the substantially horizontally oriented score 12 (FIG. 5).

Figure 8B:
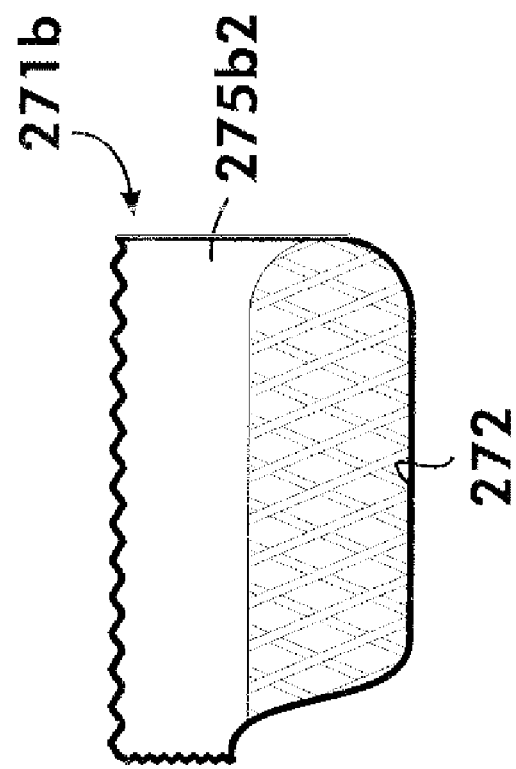
FIGS. 8A and 8B depict a front view of two lablettes, respectively, formed by breaking through the vertical score in the tablet shown in FIG. 7B.
Figure 8A:
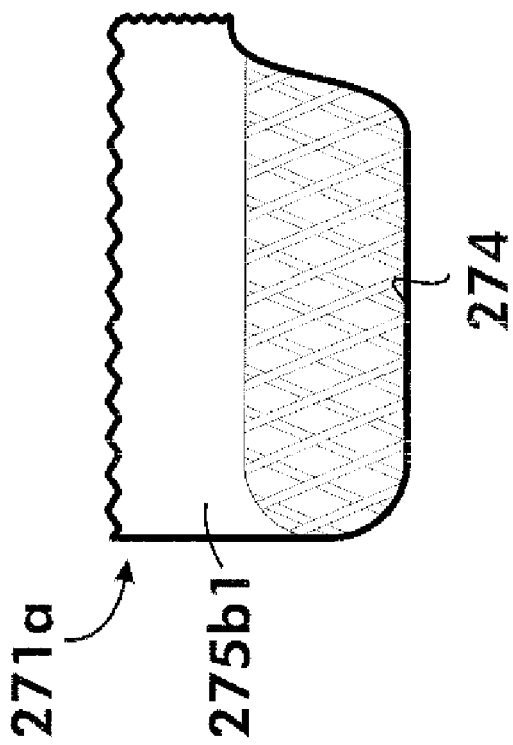

FIGS. 8A and 8B depicts the result of a second breaking, that of the tablette 271 of FIG. 7B. FIG. 8A depicts segment 274 as adjoined to new segment 275b1, formed from segment 275b of the tablette 271 of FIG. 7B. Segment 272 is unchanged horn segment 272 of the whole tablet 250 of FIG. 5, even though two breaks have occurred in tablet 250 (FIG. 5). FIG. 8B depicts tabletted 271b, comprising intact segment 272 and partial inactive segment 275b2, formed from segment 271 of FIG. 7B.

Thus, FIGS. 8A and 8B, in association with FIGS. 5, 7A, and 7B, demonstrate a means by which a combination tablet can be divided not only to separate therapeutic quantities of one active drug from another, but also then precisely give a partial dose of one of said active drugs, such as a single active drug contained in the composition forming both segment 274 and 272.

Figure 9:
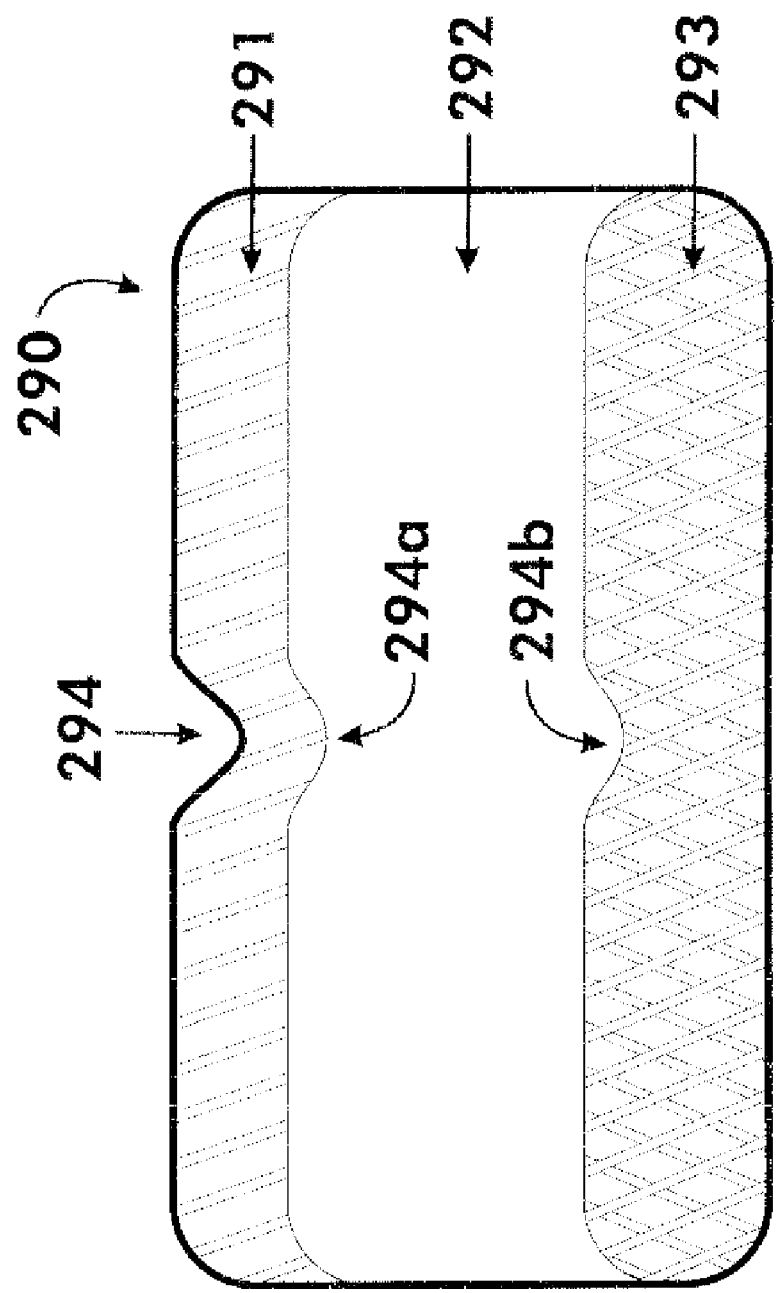
FIG. 9 depicts a cross-sectional front view of a wider-than-tall tablet having three segments, and a vertical score formed in the top end segment.

FIG. 9 depicts a cross-sectional front view of a wider-than-tall tablet 290 having three segments—upper active end segment 291, middle inactive segment 292 and lower end segment 293—and a substantially vertically oriented score 294 formed in the top surface of the upper end segment 291. Because the embossing forming the score is provided as part of the top punch used in the tablet press, the embossing and score are translated into the middle segment (294a) and the lower segment (294b). Typically, an embossing on an upper punch will not completely divide the upper segment into separate unitary segments.

Figure 10:
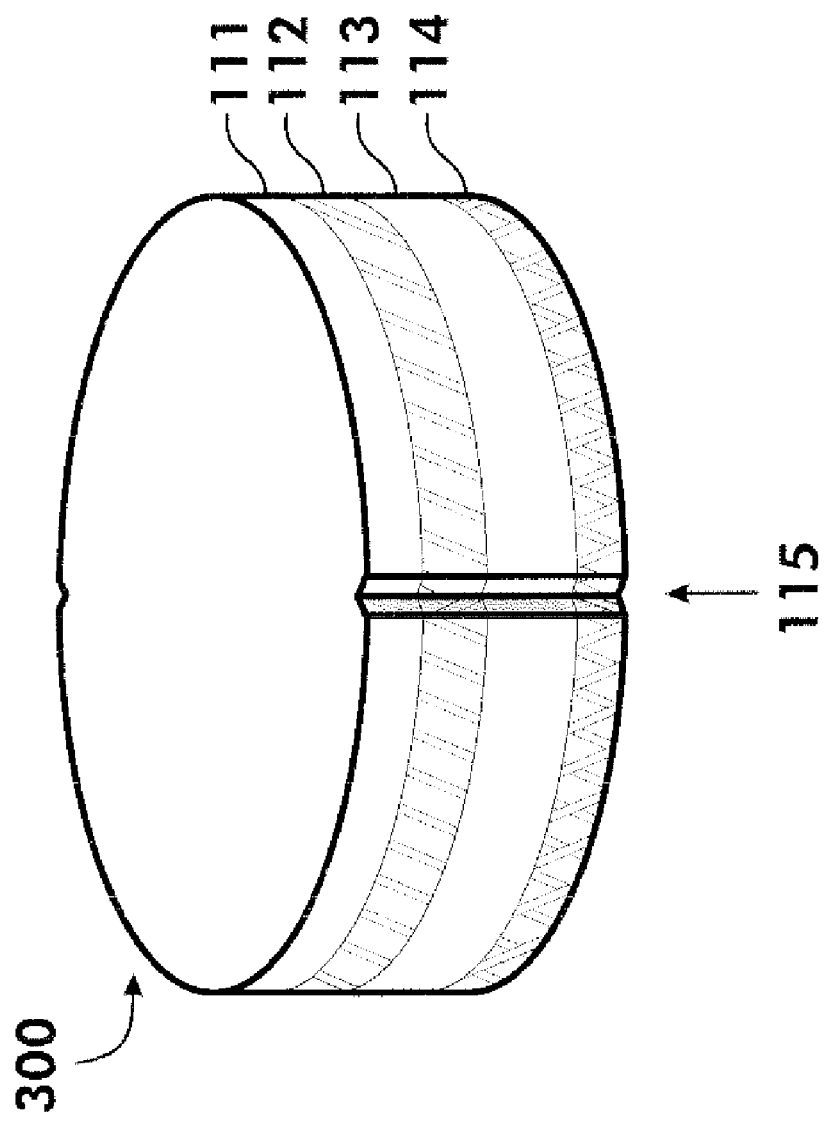
FIG. 10 depicts a perspective view of a tablet according to the subject invention having four segments, and at least one substantially vertical score in a side of the tablet.

FIG. 10 depicts a perspective view of tablet 300 having four segments—top inactive end segment 111, a middle or inner active segment 112, a middle or inner inactive segment 113, and a bottom active end segment 114. The tablet shown in FIG. 10 has a substantially vertically oriented score 115 formed in a side of the tablet. The vertical score 115 is shown traversing at least two segments of the tablet.

Benefits of the invention are not limited to tablets of any specific number of active ingredients. All segments containing an active ingredient may contain the same drug, or segments may contain different drugs. In addition, no limitation exists as to the presence of one or more additional segments created superior to (i.e., above) 277, or the composition of such. Also, though less likely, there could be another set of different unitary segments inferior to (i.e., below) segments 272 and 274.

In order to fully realize the benefits of the invention, a score may be placed into a segment (or interface between segments) of the tablet. This score may be formed in an inner segment with a file in a substantially horizontal manner, so that breaking the tablet through said score could lead to breaking through the inner segment while leaving the outer segments intact.

In addition, similar means of marking tablets may be followed such as by causing an edible ink to be placed on the tablets, thus delineating a desired region of the tablet, such as its middle segment. Such application is well known in the art. Other means of applying indicia are contemplated as within the scope of the invention.

DESCRIPTION OF MANUFACTURING PREFERRED EMBODIMENTS

Example 1

Incompatible APIs (Benazapril+Amlodipine)

A "taller than wide" tablet is made which has three segments, each with an active top or upper segment and an active lower or bottom segment separated by a substantially inactive middle segment. A Stokes 27-station tri-layer rotary tablet press is used. All formulations are directly compressible powder blends. The blending both of the amlodipine formulation and the benazepril formulation are performed in a Patterson-Kelly "V" blender. The middle segment consists of 194 mg of Nu-Tab® and requires no blending. The tablets are compressed using 0.131 inch by 0.3222 inch oval, concave tablet punches to a hardness of 35 kiloponds. The bottom segment is introduced first into the die. The tablet weight is 310 mg. Tablets so made are 8 mm tall; the inactive middle segment varies from 5-6 mm in height and a width of 4 mm. Weights in mg of the granulation comprising each segment are as follow:

| Bottom Segment | Mg. |
|---|---|
| Dibasic calcium phosphate anhydrous | 51.13 |
| Amlodipine besylate | 7.15 |
| Sodium starch glycolate (Explotab ®) | 2.48 |
| Magnesium stearate | 0.93 |
| FD&C Blue #1 Aluminum Lake | 0.31 |
| Total | 62.00 |

Manufacturing Instructions

1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

|  | Mg. |
|---|---|
| Middle Segment | |
| Nu-Tab ® (Compressible sugar 30/35 N.F.) | 194.00 |
| Top Segment | |
| Lactose 310 monohydrate | 42.03 |
| Benazepril HCl | 9.00 |
| Crospovidone | 2.16 |
| Magnesium stearate | 0.54 |
| FD&C Red #40 Aluminum Lake | 0.27 |
| Total | 54.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

Tabletting Instructions 1.
1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & Layer #2 tablets to desired combined weight of layer #1 and layer #2 weight (tablets should form a soft compact).
6. Compress the tri-layer tablet to the desired total tablet weight (layer #1 weight+layer #2 weight+4 layer #3 weight) Tablet should be at desired hardness.

Example 2

Incompatible APIs (Benazapril+Amlodipine)

A similar tablet of the invention is separately produced using the same top and bottom segments as the above, but using the following ingredients instead of Nu-Tab for the middle segment. The following are blended using a Patterson-Kelly "V" blender.

| Ingredients for middle segment: | Mg. |
|---|---|
| Dibasic calcium phosphate anhydrous | 158.59 |
| Magnesium stearate | 2.79 |
| PVP K-30 | 2.62 |
| Total | 164.00 |

Manufacturing Instructions
1. Weigh each ingredient.
2. Screen each ingredient.
3. Place all of the ingredients, except the lubricant, into a suitable mixer and mix for desired time.
4. Add the lubricant to the blend from Step #3 and mix for desired time.
5. Add the blend to a suitable press fitted with the desired tooling and compress into tablets.

The tablets were compressed using oval 0.131 inch by 0.3222 inch, concave tablet punches to a hardness of 35 kiloponds. The bottom segment was introduced first into the die. The tablet weight was 280 mg. Tablets with said middle segment were 6 mm high, and the inactive middle segment was 3.5-4 mm high.

Tabletting Instructions
1. Place the powder for active layer in hopper #1.
2. Place the powder for placebo layer in hopper #2.
3. Place the powder for active layer in hopper #3.
4. Compress layer #1 tablets to desired weight (tablets for layer #1 should form a soft compact).
5. Compress layer #1 & Layer #2 tablets to desired combined weight of layer #1 and layer #2 weight (tablets should form a soft compact).
6. Compress the tri-layer tablet to the desired total tablet weight (layer #1 weight+layer #2 weight+layer #3 weight) Tablet should be at desired hardness.

In a similar way, other taller than wide tablets can be made on a tablet press, such as, the Korsch TRP900 which can produce taller tablets due to its design for deep filling cams which allow for deeper fills and greater distances between the tipper and lower compression tools.

To make an oval 0.131 inch by 0.3222 inch, concave tablet that is 12 mm tall on the Korsch TRP900 the formulator would have to increase the weight of the inactive Nu-Tab® middle segment to about 323 mg. Similarly to have a finished tablet height of 14 mm the tablet would be formulated with a middle segment weighing about 388 mg. If the formulator preferred, they could use the second example for a middle layer, i.e., the dibasic calcium phosphate (DCP) formulation. In such a case making an oval 0.131 inch by 0.3222 inch, concave tablet that is 12 mm tall on the Korsch TRP900 the formulator would have to increase the weight of the inactive DCP middle segment to about 410 mg. Similarly to have a finished tablet height of 14 mm the tablet would be formulated with a middle segment weighing about 492 mg.

Example 3

Incompatible APIs
(Benazapril+Amlodipine)—5-Layers

Tablets containing 20 mg benazapril hydrochloride and amlodipine besylate equivalent to 5 mg of amlodipine base can be prepared as follows:

A. Benazepril Hydrochloride Granulation
Benazepril hydrochloride granulation can be prepared using the following:
1. Benazepril HCl 20.000 g
2. Lactose, monohydrate 32.920 g
3. Pregelatinized Starch 5.000 g
4. Colloidal $SiO_2$ 1.000 g
5. Crospovidine 2.000 g
6. Microcrystalline Cellulose 10,000 g
7. Hydrogenated Castor Oil 4.000 g
8. Purified Water as needed Benazepril HCl, lactose monohydrate, and pregelatinized starch will be milled and blended together and water added to granulate the blend. The wet granules will be screened and oven dried. The dried granules will then be milled together with crospovidone, microcrystalline cellulose, and hydrogenated castor oil. Colloidal $SiO_2$ will be screened and then mixed with the other ingredients. The resulting mixture is the benazapril HCl granulate.

B. Amlodipine Besylate Granulation

Amlodipine besylate granulation can be prepared using the following:
1. Amlodipine Besylate 6,944 g
2. Microcrystalline Cellulose 124,056 g
3. Calcium Phosphate Dibasic 63,000 g
4. Sodium Starch Glycolate 4,000 g
5. Magnesium Stearate 2,000 g Amlodipine besylate, microcrystalline cellulose, calcium phosphate dibasic, and sodium starch glycolate can be mixed together to form a blended mixture. The blended mixture can then be screened and blended again. Magnesium stearate can then be separately screened and then blended with said twice-blended mixture containing amlodipine. The resulting mixture is the amlodipine besylate granulate.

C. Tabletting of the Benazepril and Amlodipine Granulations.

The Korsch TRP 900 (hereinafter the "Korsch") has five filling stations and can be used to make single layer or multi-layer tablets having up to 5 layers, as desired by the tablet manufacturer. The Korsch's five feeders are placed in a rotatably circular fashion around and above the die table. The Korsch can be set so that from one (1) to five (5) of the feeders are in service during tablet manufacturing.

In the manufacture of a segmented tablet configured as $A_1$-I-I-$A_2$-I using benazapril hydrochloride as the first active ingredient ($A_1$), amlodipine besylate as the second active ingredient ($A_2$), and an inactive composition (I) comprising the amlodipine composition from Ex. 1(B), above, without active ingredient, i.e., a placebo composition, an aliquot of the first benazapril hydrochloride granulation, containing a pharmacologically effective dose of benazapril hydrochloride enters the tablet die and is tamped. Second, a granulation comprising an aliquot of the inactive granulation enters the die and is tamped. At the third tilling station, another fill of inactive granulation enters the die and is tamped. At the fourth filling station, an aliquot of the amlodipine besylate granulation containing a pharmacologically effective quantity of amlodipine besylate enters the die, and is tamped. Finally, at the fifth filling station an aliquot of the inactive granulation enters the die and is tamped. Final compression is then applied to form the five-segment benazapril hydrochloride+amlodipine besylate tablet.

Optionally, aster formation of the multi-layer tablet, a printed line or other forms of indicia such as dotted lines, symbols or perforations may be placed on or in the surface of the tablet, all of which serve the purpose of allowing identification of a breaking region.

Example 4

Compatible APIs (Chlorthalidone+Amlodipine)

Tablets containing and amlodipine besylate equivalent to 5 mg of amlodipine base call be prepared as follows:

A. Formulation of Chlorthalidone Active Blend

The following ingredients were used at the specified weight percentages to formulate a chlorthalidone active blend composition:

| Ingredient | Wt. % |
|---|---|
| chlorthalidone | 6.67 |
| dibasic calcium phosphate, anhydrous | 15.31 |
| microcrystalline cellulose PH 102 | 67.06 |
| microcrystalline cellulose PH 105 | 6.67 |
| sodium starch glycolate | 4.08 |
| Red or Blue Lake | 0.01 |
| magnesium stearate | 0.2 |
| Total | 100 |

Step 1. Mixing

A. Chlorthalidone and an equal mass of microcrystalline cellulose (MCC) PH 105 are added into a high shear mixer and mixed for 3 minutes.

b. The mixture from step a, above, is placed in a suitably sized "V" blender. MCC PH 102, sodium starch glycolate and Red or Blue Lake are added to the mixture from step a, and mixed for 15 minutes.

c. Half of the magnesium stearate is added to the mixture from step b, above, and blended for 3 minutes.

Step 2. Roller Compaction d. The blended mixture from step c is dry granulated on a suitable roller compactor, at a compression force between 8 to 12 kN/cm and at a roller speed of 3 to 6 rpm.

e. The roller-compacted material from step d is milled to a particle size suitable for tablet compression.

Step 3. Mixing of Final Active Blend f. The milled material from step e is placed in a suitably sized "V" blender. The remaining magnesium stearate is added to the blender and the material is mixed for 3 minutes to obtain the final active blend.

B. Formulation of Inactive Blend

The following ingredients are used at the specified weight percentages to formulate an inactive blend composition:

Step 1. Mixing a. The dibasic calcium phosphate, anhydrous, microcrystalline cellulose (Avicel PH 102), microcrystalline cellulose (Avicel PH 105), and sodium starch glycolate are added to a suitable "V" blender and mixed for 15 minutes.

b. The intragranular magnesium stearate is added to the mixture from step "a," and blended for 3 minutes.

Step 2. Roller Compaction c. The blended mixture from step "b" is dry granulated on a suitable roller compactor, at a compression force between 8 to 12 kN/cm and at a roller speed of 3 to 6 rpm.

d. The roller-compacted material from step "d" is milled to a particle size suitable for tablet compression. The compression force is between 8 to 12 kN/cm at a roller speed of 3 to 6 rpm.

Step 3. Final Blending e. The milled material is added to a suitably sized "V" blender. The remaining magnesium stearate is added to the blender and the material is mixed 3 minutes.

| Ingredient | Wt. % (granulation) | Wt. % (Final Blend) |
|---|---|---|
| dibasic calcium phosphate, anhydrous (1:4 ratio with Avicel PH 102) | 17.443 | 17.426 |
| microcrystalline cellulose (Avicel PH 102) | 69.773 | 69.703 |

-continued

| Ingredient | Wt. % (granulation) | Wt. % (Final Blend) |
|---|---|---|
| microcrystalline cellulose (Avicel PH 105) | 8.580 | 8.571 |
| sodium starch glycolate | 4.004 | 4.000 |
| magnesium stearate (intragranular) | 0.200 | 0.200 |
| magnesium stearate (extragranular) | — | 0.200 |
| Total | 100.000 | 100.000 |

C. Amlodipine Besylate Granulation
Amlodipine besylate granulation can be prepared using the following:
1. Amlodipine Besylate 6.944 g
2. Microcrystalline Cellulose 124.056 g
3. Calcium Phosphate Dibasic 63.000 g
4. Sodium Starch Glycolate 4.000 g
5. Magnesium Stearate 2.000 g Amlodipine besylate, microcrystalline cellulose, calcium phosphate dibasic, and sodium starch glycolate can be mixed together to form a blended mixture. The blended mixture can then be screened and blended again. Magnesium stearate can then be separately screened and then blended with the twice-blended mixture containing the amlodipine. The resulting mixture is the amlodipine besylate granulate.

D. Tabletting of the Chlorthalidone and Amlodipine Granulations.

The Korsch TRP 900 (hereinafter the "Korsch") has five filling stations and can be used to make single layer or multi-layer tablets having up to 5 layers, as desired by the tablet manufacturer. The Korsch's five feeders are placed in a rotatably circular fashion around and above the die table. The Korsch can be set so that firm one (1) to five (5) of the feeders are in service during tablet manufacturing.

In the manufacture of a five-segment tablet configured as $A_1$-I-I-$A_2$-I using chlorthalidone as the first active ingredient ($A_1$), amlodipine besylate as the second active ingredient ($A_2$), and the inactive blend as inactive composition (I), an aliquot of the first chlorthalidone granulation, containing a pharmacologically effective dose of chlorthalidone enters the tablet die and is tamped. Second, an aliquot of the inactive blend enters the die and is tamped. At the third filling station, another fill of inactive blend enters the die and is tamped. At the fourth filling station, an aliquot of the amlodipine besylate granulation containing a pharmacologically effective quantity of amlodipine besylate enters the die, and is tamped. Finally, at the fifth filling station an aliquot of the inactive blend enters the die and is tamped. Final compression is then applied to form the five-segment chlorthalidone+amlodipine besylate tablet.

Optionally, after formation of the multi-layer tablet, a printed line or other forms of indicia such as dotted lines, symbols or perforations may be placed on or in the surface of the tablet, all of which serve the purpose of allowing identification of a breaking region.

The invention also includes the method of administering one or more drugs via the dosage forms such as tablets and tablettes of the invention to a patient, mammal, or other animal in need of pharmaceuticals for the prevention or treatment of an illness, maintenance of good health, retarding of aging, or other purpose. Included are methods of treating a patient with only one drug from a combination product, such as with a novel tablette of the invention, enabling downward dose adjustment for a variety of reasons; or, in a similar vein, a patient may be treated with one whole tablet containing a plurality of active drugs and in addition receive only one drug from a similar tablet, thus enabling upward dose adjustment. Combination products that can benefit from the invention, in which one drug is in an outer active segment, and a second and different drug is in the other outer active segment, and an inactive middle segment as in embodiments such as was described in paragraphs 3 and 4 above, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial dose of medication from a whole tablet, which may be a half or quarter of the whole dose, but may usefully be a different fraction. Warfarin especially may usefully be produced and dosed according to the invention with separable segments of the tablet that may but need not be as halves, quarters, etc. L-thyroxine and digoxin are other examples that could so benefit, along with warfarin.

The following give possible clinical situations in which the tablets of the invention could provide important benefits.

1. A currently marketed product in the United States is Caduet®, which contains the active ingredients atorvastatin calcium (atorvastatin) and amlodipine besylate (amlodipine) which are largely homogeneously interdispersed in an unscored tablet. The product is indicated to treat both hyperlipidemia (atorvastatin) and hypertension (amlodipine). A patient ingesting this tablet daily may then undergo a blood test and be diagnosed as having liver dysfunction as manifested by elevation of an enzyme's concentration in the blood. The physician may then recommend cessation, possibly temporary, of atorvastatin, which is stated by the manufacturer to be a possible cause of liver dysfunction. A patient receiving Caduet, however, would have to thus also discontinue amlodipine, which is not in this example desired by the physician. A tablet of the invention in which atorvastatin and amlodipine were segregated in different outer active segments, separated by a middle segment of adequate dimensions, would be a clear advance over the current Caduet formulation, because such a tablet would allow a patient to promptly continue ingesting amlodipine while stopping ingestion of atorvastatin, without having to go to a pharmacy and fill a new prescription for a tablet containing only amlodipine as the active ingredient, while having previously had the convenience of having both drugs combined in a single dosage form. The above embodiment of the invention represents an improvement over the current Caduet dosage form.

Another clinical situation in which the invention is superior to Caduet is one in which a patient receiving amlodipine 5 mg once daily and atorvastatin 20 mg once daily is advised by a physician to increase the daily amlodipine dose to 10 mg once daily. A patient in possession of adequate tablets of the invention, with the active drugs segregated in a three-segment tablet, would be able to promptly increase the amlodipine dose by taking a whole tablet of the invention once daily, plus a tablette containing 5 mg of amlodipine, produced by breaking a second whole tablet of the invention.

Another clinical situation in which the invention is superior to Caduet involves the case in which a physician wishes a patient to ingest atorvastatin 20 mg each morning and amlodipine 2.5 mg twice daily. The invention provides for amlodipine to be separated from atorvastatin and then broken precisely in half. The invention thus allows the patient the advantage of one tablet whereas to accomplish this currently in the United States would require one 20 mg Lipitor® (atorvastatin) tablet and two Norvasc (amlodipine) 2.5 mg tablets.

2. The combination of amlodipine besylate and benazepril hydrochloride (benazepril) is marketed in the United States under the brand name of Lotrel®. This product is a capsule that is routinely ingested whole. An embodiment of the invention provides a whole tablet containing one outer segment containing amlodipine as the only active drug and the other outer segment containing benazepril as the only outer drug. If desired, either outer layer may be formed into more than one segment, as in FIG. 1a. As in example 1 above regarding Caduet, the middle segment is inactive and may be broken through to create two tablettes, each comprising a whole amount of each outer active segment plus approximately half of the amount of the middle inactive segment. If a patient were to develop a need for double the dose of one active drug but not the other, the tablet of the invention could meet that need. Alternatively, if a patient were to develop a need to ingest only one active drug, possibly temporarily, due to such conditions as blood pressure changes or a side effect to one drug but not the other, the tablet of the invention allows this to be done without a new dosage form being prescribed.

3. Another use of the invention involves the combination of amlodipine and chlorthalidone or another diuretic, which may usefully be combined to treat hypertension. Benefits of the invention are similar to those described in the paragraph immediately preceding this paragraph.

4. Another use of the invention involves the combination of olmesartan medoxomil (olmesartan, an angiotensin receptor blocker) and hydrochlorothiazide (HCTZ). This product is currently marketed in the United States under the name Benicar/HCT®, with the doses, respectively, of, in mg: 20/12.5, 40/12.5, and 40/25. A very common starting dose of a patient will be 20/12.5 once daily. The product is currently marketed in all strengths as a homogeneous tablet containing both active drugs. Formulated according to the current invention, a patient who begins treatment with the 20/12.5 dose may be increased with the same tablet to each of the other doses by ingesting one whole 20/12.5 tablet and either a half tablet containing 20 mg of olmesartan or a half tablet containing 25 mg of HCTZ. This will provide the physician an opportunity to investigate the new dose before giving the patient a new prescription. Other advantages of the invention are similar to those described above.

5. Another useful combination product that may be formulated according to the invention involves angiotensin converting enzyme inhibitors (ACEs) and diuretics such as HCTZ. Both types of drug not uncommonly have side effects, so that the invention will be useful to physicians in dealing with the side effects, as well as with changing dosing needs to deal with the anti-hypertensive and other clinical benefits of the drugs.

6. Another product that may benefit from the invention regarding separating active drugs in separate outer layers with an inactive middle segment (layer) is a combination product containing two active drugs, fluoxetine and olanzapine.

No limitation to the above therapeutic fields or to the specific examples within their fields is intended for tablets of the invention, which may be used in any suitable combination of drugs. No limitation to two-drug combinations exists, as well. For instance, one outer active segment of a tablet according to the invention could contain levodopa and carbidopa, and the other outer active segment could contain entacapone, a tablet product containing all three drugs in a homogeneous fashion that is currently marketed in the United States as Stalevo®. Also, a tablet per the invention could involve five layered segments, with, for example, amlodipine in one outer segment, an inactive segment adjoining it, a middle segment containing chlorthalidone or HCTZ, and a second inactive Segment adjoining both it and the other outer segment that contains benazepril (see FIG. 8). If both inactive segments were of adequate dimensions to be conveniently breakable without damaging any of the three active segments, thus providing significant clinical advantages due to the adoption of flexible dosing of the different active segments.

The following list of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drugs from within the following six drug classes.

In addition, tablets of the invention may be created containing only one of a drug from the following list. With regards to combination use, two methods of use may apply to the invention. One of these methods is to place an individual drug in a granulation and a different individual drug (or combination of drugs) in a different granulation, potentially with an inactive granulation interposed between them; another method is to place a plurality of drugs in one or more segments.

1. Anti-anginal agents, for example:
   A. Calcium antagonists (see list below);
   B. Beta-blocker (see list below);
   C. Organic nitrate preparation (e.g., isosorbide mononitrate or dinitrate), 2. Anti-anginal agent plus an anti-platelet agent, such as aspirin, clopidogrel, or ticlopidine.

3. Two hypoglycemic agents (see list below).

4. Potassium chloride and any thiazide-type or loop diuretic (see lists below).

5. Lipid-lowering agent plus: hypoglycemic agent, anti-platelet agent, anti-anginal agent, and/or antihypertensive agent (see lists above and below).

Hypoglycemic Agents Include:
   thiazolidinediones: pioglitazone, rosiglitazone; sulfonylureas: glyburide, glipizide, glimepiride, chlorpropamide:
   Biguamides: metformin;
   Meglitinides: nateglinide, repaglinide;
   Glucosidase inhibitors: acarbose, miglitol.

6. Antihypertensive agents:
   Beta-blockers: acebutolol, atenolol, bisoprolol, celiprolol, metoprolol, mebivolol, carvedilol (a mixed alpha-beta blocker), nadolol, oxprenolol, penbutolol, pindolol, propranolol, timolol, betaxolol, carteolol;
   Calcium antagonists (calcium-channel blockers): nifedipine, amlodipine, verapamil, diltiazem, nisoldipine, felodipine, isradipine, lacidipine, lercanidipine, nicardipine, manidipine;
   Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
   Angiotensin converting enzyme inhibitors: captopril, enalapril, lisinopril ramipril, trandolapril, quinapril, perindopril, moexipril, benazepril, fosinopril;

Angiotensin receptor blockers: losartan, valsartan, candesartan, telmisartan, eprosartan, irbesartan;

High-ceiling (loop) diuretics (with or without potassium-retaining diuretics such as triamterene, amiloride, or spironolactone): furosemide, torsemide, ethacrynic acid, bumetamide;

Aldosterone antagonist diuretics: spironolactone, eplerenone;

Alpha-blockers: doxazosin, terazosin prazosin, indoramin, labetolol (a mixed alpha-beta blocker);

Central alpha-agonists: clonidine, methyldopa;

Imidazoline: moxonidine;

Direct vasodilators: hydralazine, in minoxidil;

Adrenergic neuronal blocker: guanethidine.

Lipid-lowering agents include:

Statins: lovastatin, simvastatin, pravastatin, rosuvastatin, atorvastatin, fluvastatin;

Fibrates: clofibrate, bezafibrate, fenofibrate, gemfibrozil, ciprofibrate;

Others: ezetimide, niacin, acipimox.

The combinations of drugs disclosed herein are for illustrative purposes and are not intended to limit the scope of the invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are however but a small fraction of the great mass of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

1. Warfarin is an anticoagulant marketed in the U.S. under the brand name Coumadin®, which is a scored tablet. Research has shown that patients do not break warfarin 5 mg tablets into equal 2.5 mg segments. The invention teaches different types of tablets that allow warfarin tablets of any common human dose to be broken into precise halves, and potentially precise thirds, quarters, etc. Thus a patient may utilize warfarin half-tablets produced as per the invention with similar confidence as in the whole tablet. Because warfarin closes are frequently broken, many clinical scenarios exist in which the invention will benefit patients.

2. Norvasc (amlodipine besylate or amlodipine herein) is marketed as unscored 2.5, 5, and 10 mg tablets in the U.S. These tablets are of irregular shape and are difficult to break. The FDA-approved dosage range is from 2.5 to 10 mg ingested orally daily. The invention allows improved functionality of amlodipine. For example, under the invention, a patient receiving 5 mg daily who a physician wishes to increase to 7.5 mg daily may simply utilize a tablet of the invention that comprises two separate 2.5 mg segments to increase the dose to precisely 7.5 mg, such as by ingesting one whole 5 mg tablet and one 2.5 mg tablette created by breaking a 5 mg tablet into two tablettes each containing 2.5 mg of amlodipine. Convenience and cost savings are clear. Similarly, a patient receiving a 10 mg dose of Norvasc who is advised to reduce the dose to 5 mg daily must currently purchase a new prescription for 5 mg Norvasc tablets. The invention provides the ability to provide a 10 mg tablet that may be broken into two tablettes, each containing precisely 5 mg of amlodipine. The invention may therefore enable greater flexibility of treating patients, and provide cost savings as well. A further benefit of the invention is that various embodiments allow fully accurate separation of a tablet into a tablette comprising one-fourth of the dose of the active ingredient as is found in the whole tablet. This may be done for amlodipine by providing four active segments all containing 2.5 mg amlodipine and all contiguous with the same side of an inactive outer segment. Thus, a 10 mg amlodipine tablet of the invention may be utilized to provide a 7.5 mg dose; or, it may be utilized to provide four 2.5 mg doses.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg daily.

Another use of the invention is to for the first time enable a method of cost savings to insurers and patients. The invention allows this because many drugs, such as Norvasc and Coumadin, have pricing that differs little (if at all) between different doses. Because tablet splitting is imprecise for most scored tablets, the practice of mandatory splitting has been met with disapproval by most physician and pharmacist organizations. The invention enables tablet splitting due to provide accurate dosing when a tablet (or some tablettes, as in FIG. 1b) of the invention are broken as described herein. In addition, the ability to separate one active drug from another in a combination product has cost saving advantages, as well.

It is recognized that related inventions may be within the spirit of the disclosures herein. Also no omission in the current application is intended to limit the inventors to the current claims or disclosures. As this application is a continuation-in-part of pending U.S. patent applications Ser. No. 11/569,343; Ser. No. 10/598,267; and Ser. No. 10/598,306, each of which claims priority to U.S. Provisional Appl'n Ser. No. 60/573,042 filed May 21, 2004 and U.S. Provisional Appl'n Ser. No. 60/573,134 filed May 21, 2004, these applications are hereby incorporated by reference in their entirety as applicable. While certain preferred and alternative embodiments of the invention have been set forth for purposes of disclosing the invention, modifications to the disclosed embodiments may occur to those who are skilled in the art.

We claim:

1. A compressed, immediate-release pharmaceutical tablet containing a pharmaceutically effective dose of each of two or more active pharmaceutical ingredients, said tablet having a tablet height greater than tablet width said tablet height being measured vertically from a highest top point of said compressed tablet to a lowest bottom point of said compressed tablet and said width being measured as a greatest horizontal dimension of the tablet halfway between the highest point and the lowest point of said compressed tablet, except that when a horizontal cross-section of said tablet is substantially rectangular, the width is a length of a long axis of said rectangle, said tablet consisting essentially of:
- a first composition forming a bottom layered segment or a plurality of compositionally substantially identical segments forming an exposed bottom end surface of the tablet, said segment or segments having an exposed outer side surface and a contacting face located opposite and superior to the exposed bottom end stirface of the tablet, said first composition consisting essentially of excipients having immediate-release characteristics and a pharmaceutically effective dose of at least one active pharmaceutical ingredient;
- a second composition forming a top layered segment forming an exposed top end surface of the tablet, said segment having an exposed side surface and a lower contacting face opposite and inferior to the exposed top end surface, said second composition consisting essentially of excipients having immediate-release characteristics and a pharmaceutically effective dose of at least one active pharmaceutical ingredient, wherein, said first and second compositions are pharmaceutically compatible with one another and have at least one different active pharmaceutical ingredient;
- a third composition consisting essentially of excipients having immediate-release characteristics and being substantially free of active pharmaceutical ingredient, said composition forming a middle layered segment having a lower contacting face in contact with the bottom end segment or segments, an exposed outer side surface, and an upper contacting face in contact with top end segment, said middle segment having, after compression, an effective height of at least 2 mm, wherein the effective height is the vertical distance between a highest point of the bottom end segment or segments and a lowest point of said top end segment, said middle segment having a height or exposed side surface of at least 3 mm, said height of the middle segment being a vertical distance between the upper and lower contacting faces of the middle segment, and said middle segment further having a substantially horizontal score formed therein, transverse to the vertical axis of the tablet; and
- optionally, an immediate-release coating substantially free of active pharmaceutical ingredient; wherein the terms "bottom," "top," "end," "middle," "side," "outer," "superior," "inferior," "lower," "upper," "vertical," and "horizontal" refer to a spatial orientation of said tablet as oriented in a tablet die in which compression occurs.

2. The tablet of claim 1 wherein the orientation of said score is such that a plane that would pass through said score is about halfway between a highest and lowest point of said tablet.

3. The tablet of claim 1 wherein a substantially horizontal score or printed indicia is about equidistant from a highest point of the bottom segment and a lowest point of the top segment.

4. The tablet of claim 1 wherein the tablet is uncoated.

5. The tablet of claim 1 wherein said tablet has a coating comprising a water-soluble polymer.

6. The compressed pharmaceutical tablet of claim 1 comprising an active pharmaceutical ingredient selected from the group consisting of a calcium channel blocker, an angiotensin converting enzyme inhibitor, and a diuretic.

7. The compressed pharmaceutical tablet of claim 6 comprising a calcium channel blocker selected from the group consisting of amlodipine, verapamil, diltiazem, nisoldipine, felodipine, isradipine, lacidipine, lercanidipine, nicardipine, manidipine, and nifedipine, or a pharmaceutically acceptable salt, derivative, hydrate, isomer, polymorph, pro-drug, or metabolite thereof.

8. The compressed pharmaceutical tablet of claim 6 comprising an angiotensin converting enzyme inhibitor selected from the group consisting of captopril, enalapril, lisinopril, ramipril, trandolapril, quinapril, perindopril, moexipril, benazepril, and fosinopril, or a pharmaceutically acceptable salt, derivative, hydrate, isomer, polymorph, pro-drug, or metabolite thereof.

9. The compressed pharmaceutical tablet of claim 6 comprising a pharmaceutically effective amount of chlorthalidone, or a pharmaceutically acceptable salt, derivative, hydrate, isomer, polymorph, prodrug, or metabolite thereof.

10. The compressed tablet of claim 1 wherein one of said first or second composition contains amlodipine or a pharmaceutically acceptable salt, derivative, hydrate, isomer, polymorph, pro-drug, or metabolite thereof as the active pharmaceutical ingredient, and the other of said first or second composition contains benazapril or a pharmaceutically acceptable salt, derivative, hydrate, isomer, polymorph, pro-drug, or metabolite thereof as the active pharmaceutical ingredient.

11. The compressed tablet of claim 1 wherein one of said first or second composition contains amlodipine or a pharmaceutically acceptable salt, derivative, hydrate, isomer, polymorph, pro-drug, or metabolite thereof as the active pharmaceutical ingredient, and the other of said first or second composition contains chlorthalidone or a pharmaceutically acceptable salt, derivative, hydrate, isomer, polymorph, pro-drug, or metabolite thereof as the active pharmaceutical ingredient.

* * * * *